(12) United States Patent
Verwaerde et al.

(10) Patent No.: US 6,703,214 B2
(45) Date of Patent: Mar. 9, 2004

(54) LIPID UPTAKE ASSAYS

(75) Inventors: Philippe Verwaerde, Neuville En Ferrain (FR); Cindy Anthonissen, Denderhoutem (BE); Benoit Deprez, Lille (FR); Beatrice Bonnet, Lille (FR); Thierry Bogaert, Kortrijk (BE)

(73) Assignee: Devgen NV, Zwijnaarde (BE)

( * ) Notice: Subject to any disclaimer, the term of this patent is extended or adjusted under 35 U.S.C. 154(b) by 0 days.

(21) Appl. No.: 09/861,881

(22) Filed: May 21, 2001

(65) Prior Publication Data

US 2002/0137205 A1 Sep. 26, 2002

(30) Foreign Application Priority Data

May 19, 2000 (GB) .............................. 0012229

(51) Int. Cl.[7] ................................ C12Q 1/44
(52) U.S. Cl. ........................ 435/19; 435/23; 435/375
(58) Field of Search ........................ 435/19, 23, 375, 435/968; 436/71, 172

(56) References Cited

U.S. PATENT DOCUMENTS

| | | | |
|---|---|---|---|
| 4,774,339 A | | 9/1988 | Haugland et al. |
| 5,274,113 A | | 12/1993 | Kang et al. |
| 5,338,854 A | | 8/1994 | Kang et al. |
| 5,929,062 A | * | 7/1999 | Haines ................. 514/182 |
| 5,994,063 A | * | 11/1999 | Metzker et al. ........... 435/6 |
| 6,114,177 A | * | 9/2000 | Naguib ................. 436/172 |
| 6,323,186 B1 | * | 11/2001 | Klaubert et al. .......... 514/47 |
| 6,342,379 B1 | * | 1/2002 | Tsien et al. ........... 435/173.4 |
| 6,348,321 B1 | * | 2/2002 | Stahl et al. ............. 435/7.21 |

FOREIGN PATENT DOCUMENTS

| | | | |
|---|---|---|---|
| WO | WO 99/31267 | * | 6/1999 |
| WO | WO 00/01846 | | 1/2000 |
| WO | WO 00/63425 | | 10/2000 |
| WO | WO 00/63427 | | 10/2000 |

OTHER PUBLICATIONS

Matyash V. Distribution and Transport of Cholesterol in *C. elegans*. Molecular Biology of the Cell. 12:1725–36, Jun. 2001.*
Furlong S. Uptake and Compartmentalization of Fluorescent Lipid Analogues in *Larval S. mansoni*. J of Lipid Research 36(1)1–12, 1995.*
Haughland Handbook of Fluorescent Probes, 6th ed., Chapter 13 Fluroescent Phospholipids, Fatty Acids and Sterols, 1996, pp. 287–308.*
Aspbury R. Fatty Acylation of Polypeptides in the Nematode *C. elegans*. Biochimica et Biophysica Acta 1382(1998)111–119.*
Hendrickson H. Intramolecularly Quenched BODIPY . . . Anal Biochem 276, 27–35, 1999.*
Watts et al., *Am. J. Clin. Nutrition* 64: 202–209 (1996).
Storlien et al., *Science* 237: 885–888 (1987).

Stahl et al., *Mol. Cell Biol.* 4: 299–308 (1999).
Fitscher et al., GenBank accession No. AF055899 (Feb. 02, 1999) citation only.
Glenney, J.R., Jr., GenBank accession No. NM_001233 (Oct. 31, 2000) citation only.
*C. elegans* database of the Sanger Centre, accession No. F28D1.9 (GenBank No. Z70684).
*C. elegans* database of the Sanger Centre, accession No. C56A3.7 (GenBank No. Z77655).
*C. elegans* database of the Sanger Centre, accession No. Y49E10.20 (GenBank No. Z98866).
*C. elegans* database of the Sanger Centre, accession No. W02D3.7 (GenBank No. AF003141).
Oquendo et al., GenBank accession No. P16671 (Aug. 20, 2001).
Birkenmeier et al., GenBank accession No. NM_001445 (Oct. 31, 2000).
Klucken et al., *Proc. Natl. Acad. Sci. USA* 97: 817–822 (2000).
Stangl et al., *J. Biol. Chem.* 274: 32692–32698 (1999).
Izzat et al., *J. Pharmacol. and Exp. Therap.* 293: 315–320 (2000).
Fire et al., *Nature* 391: 806–811 (1998).
Timmons and Fire, *Nature* 395: 854 (1998).
Haughland, Chap. 13, *Handbook of Fluorescent Probes and Research Chemicals* (6th edition).
Shin et al., *East Coast Worm meeting abstract* 171 (1998).
White et al., *Worm Breeder's Gazette* 1(1):17.
Hevelone et al. (1988) *Biochem. Genet.* 26:447–461.
Ellis and Horvitz, *Worm Breeder's Gazette* 7(2):44.
Babu, *Worm Breeder's gazette* 1(2):10.
Driscoll, *Brain Pathol.* 6:411–425 (1996).
Ellis et al., *Genetics* 129:79–94 (1991).
Hendrickson et al. *Anal. Biochemistry*, 1999, 276:27–35.
Thuren et al. *Anal. Biochemistry*, 1998, 170:248–255.
Biederer et al., GenBank accession No. NM_001234 (Oct. 31, 2000).
Glenney, J.R., Jr., GenBank accession No. NM_001753 (Feb. 22, 2001).
Chan et al., GenBank accession No. NM_001443 (Oct. 31, 2000).
Chan et al., GenBank accession No. M10617 (Nov. 08, 1994).
*C. elegans* database of the Sanger Centre, accession No. D1009.1a (GenBank No. U40938).
*C. elegans* database of the Sanger Centre, accession No. D1009.1b (GenBank No. U40938).
*C. elegans* database of the Sanger Centre, accession No. T13F2.8 (GenBank No. Z81122).

(List continued on next page.)

Primary Examiner—Ralph Gitomer
(74) Attorney, Agent, or Firm—Wolf, Greenfield & Sacks, P.C.

(57) ABSTRACT

The invention relates to the use of microscopic nematodes such as *C. elegans* in functional high throughput in vivo assays suitable for the detection of inhibitors or activators of intestinal lipid uptake.

16 Claims, 13 Drawing Sheets

OTHER PUBLICATIONS

*C. elegans* database of the Sanger Centre, accession No. Y76A2B.6 (GenBank No. AL032658).
*C. elegans* database of the Sanger Centre, accession No. W02D3.5 (GenBank No. AF003141).
*C. elegans* database of the Sanger Centre, accession No. T22G5.2 (GenBank No. Z81127).
*C. elegans* database of the Sanger Centre, accession No. F40F4.2 (GenBank No. U40420).
Bird, A.F., *J Neumatol* 11(1): 103–105 (1979).
Hendrickson et al., *Anal Biochem* 276: 27–35 (1999).
Matyash et al., *Mol Biol Cell* 12: 1725–1736 (2001).
Rand and Johnson, *Methods in Cell Biol* 48: 187–204 (1995).
Hui and Bernlohr, *Frontiers in Bioscience* 2: d222–231 (1997).
Haitzer et al., *J. Environ. Monit. 2: 145–149 (2000)*.
Aspury et al., *Biochim. et Biophys. Acta* 1382: 111–119 (1998).

* cited by examiner

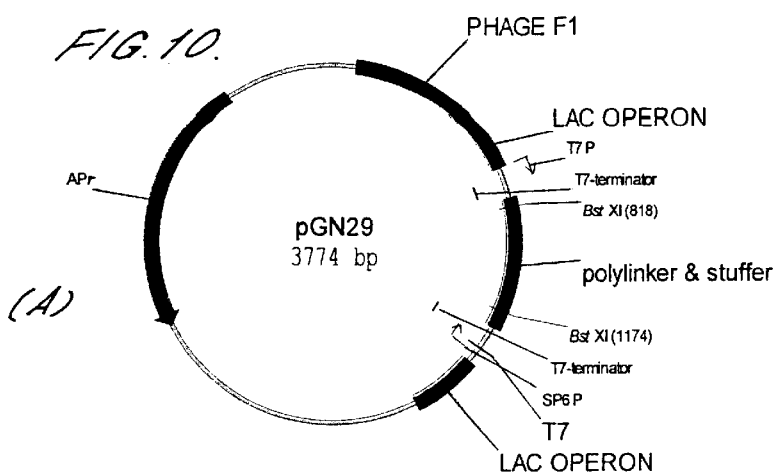
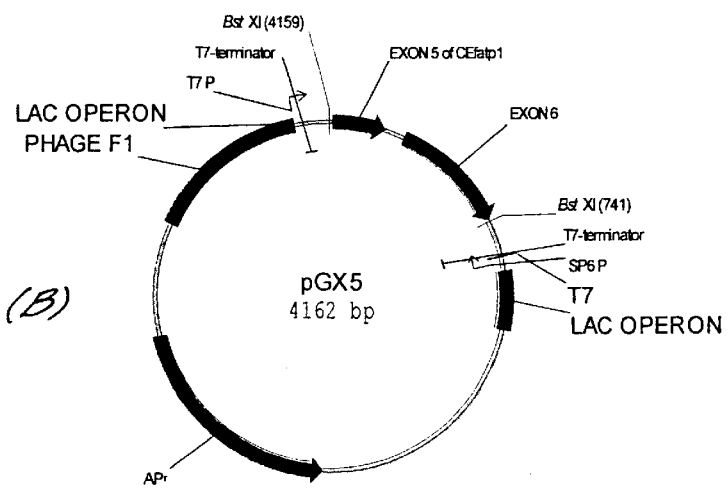
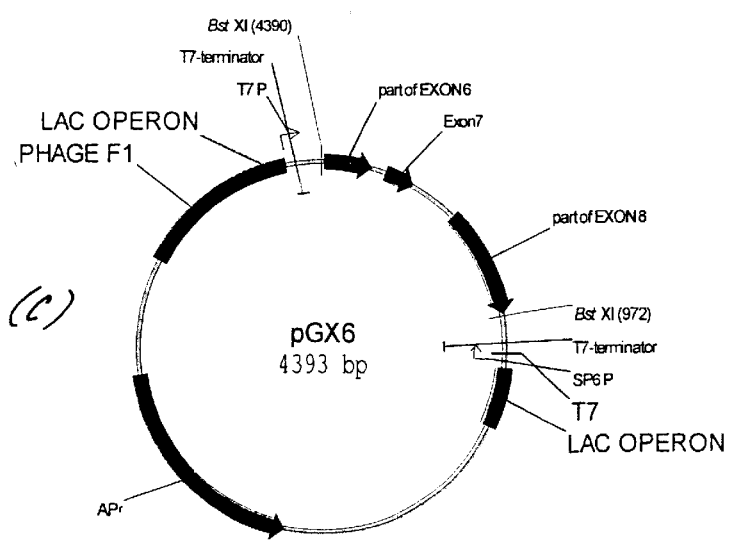
FIG. 10.

Nucleotide Sequence of pGX5:   *FIG. 14.*

```
gtgaaggttacaaaatgggcgacgttgtcgctttgtttatggaaaatagcatcgacttctttgcaatttggctgg
gactttccaagattggagtcgtgtcggcgttcatcaactcaaacttgaagttggagccattggcacattcgatta
atgtttcgaagtgcaaatcatgcattaccaatatcaatctgttgccgagtaagtttgcagaaataaatataccgg
gatgtttaaaaatcctgcgtggaaatggcagatgttttacatactattttacagtgttcaaagccgctcgtgaa
aagaatctgatcagtgacgagatccacgtgtttctggctggaactcaggttgatggacgtcatagaagtcttcag
caagatctccatcttttctctgaggatgaacctccagttatagacggactcaattttagaagcgttctgtgttat
atttacacttccggtactaccggaaatccaaagccagccgtcattaaacacttccgttacttctggattgcgatg
ggagcaggaaaagcatttggaattaataagtcagacgttgtgtacattacgatgccaatgtatcactctgccgcc
ggtatcatgggtattggatcattaattgcattcgggtcgaccgctgttattaggaaaaagttttcggcaagcaac
ttctggaaagattgcgtcaagtacaacgtcacagcgacacagtacattggagaaatcccagcacaatggatctcg
agggatcttccatacctaccagttctgcgcctgcaggtcgcggccgcgactctctagacgcgtaagcttactagc
ataacccttggggcctctaaacgggtcttgaggggttttttgagcttctcgccctatagtgagtcgtattacag
cttgagtattctatagtgtcacctaaatagcttggcgtaatcatggtcatagctgtttcctgtgtgaaattgtta
tccgctcacaattccacacaacatacgagccggaagcataaagtgtaaagcctggggtgcctaatgagtgagcta
actcacattaattgcgttgcgctcactgcccgctttccagtcgggaaacctgtcgtgccagctgcattaatgaat
cggccaacgcgcggggagaggcggtttgcgtattgggcgctcttccgcttcctcgctcactgactcgctgcgctc
ggtcgttcggctgcggcgagcggtatcagctcactcaaaggcggtaatacggttatccacagaatcaggggataa
cgcaggaaagaacatgtgagcaaaaggccagcaaaaggccaggaaccgtaaaaaggccgcgttgctggcgttttt
ccataggctccgcccccctgacgagcatcacaaaaatcgacgctcaagtcagaggtggcgaaacccgacaggact
ataaagataccaggcgtttccccctggaagctccctcgtgcgctctcctgttccgaccctgccgcttaccggata
cctgtccgcctttctcccttcgggaagcgtggcgctttctcatagctcacgctgtaggtatctcagttcggtgta
ggtcgttcgctccaagctgggctgtgtgcacgaaccccccgttcagcccgaccgctgcgccttatccggtaacta
tcgtcttgagtccaacccggtaagacacgacttatcgccactggcagcagccactggtaacaggattagcagagc
gaggtatgtaggcggtgctacagagttcttgaagtggtggcctaactacggctacactagaaggacagtatttgg
tatctgcgctctgctgaagccagttaccttcggaaaaagagttggtagctcttgatccggcaaacaaaccaccgc
tggtagcggtggtttttttgtttgcaagcagcagattacgcgcagaaaaaaaggatctcaagaagatcctttgat
cttttctacggggtctgacgctcagtggaacgaaaactcacgttaagggattttggtcatgagattatcaaaaag
gatcttcacctagatccttttaaattaaaaatgaagttttaaatcaatctaaagtatatatgagtaaacttggtc
tgacagttaccaatgcttaatcagtgaggcacctatctcagcgatctgtctatttcgttcatccatagttgcctg
actccccgtcgtgtagataactacgatacgggagggcttaccatctggccccagtgctgcaatgataccgcgaga
cccacgctcaccggctccagatttatcagcaataaaccagccagccggaagggccgagcgcagaagtggtcctgc
aactttatccgcctccatccagtctattaattgttgccgggaagctagagtaagtagttcgccagttaatagttt
gcgcaacgttgttggcattgctacaggcatcgtggtgtcacgctcgtcgtttggtatggcttcattcagctccgg
ttcccaacgatcaaggcgagttacatgatcccccatgttgtgcaaaaaagcggttagctccttcggtcctccgat
cgttgtcagaagtaagttggccgcagtgttatcactcatggttatggcagcactgcataattctcttactgtcat
gccatccgtaagatgcttttctgtgactggtgagtactcaaccaagtcattctgagaataccgcgccggcgacc
gagttgctcttgcccggcgtcaatacgggataatagtgtatgacatagcagaactttaaaagtgctcatcattgg
aaaacgttcttcggggcgaaaactctcaaggatcttaccgctgttgagatccagttcgatgtaacccactcgtgc
acccaactgatcttcagcatcttttactttcaccagcgtttctgggtgagcaaaaacaggaaggcaaaatgccgc
aaaaaagggaataagggcgacacggaaatgttgaatactcatactcttccttttcaatattattgaagcattta
tcagggttattgtctcatgagcggatacatatttgaatgtatttagaaaaataaacaataggggttccgcgcac
atttccccgaaaagtgccacctgacgtctaagaaaccattattatcatgacattaacctataaaaataggcgtat
cacgaggccctttcgtctcgcgcgtttcggtgatgacggtgaaaacctctgacacatgcagctcccggagacggt
cacagcttgtctgtaagcggatgccgggagcagacaagcccgtcagggcgcgtcagcgggtgttggcgggtgtcg
gggctggcttaactatgcggcatcagagcagattgtactgagagtgcaccatatgcggtgtgaaataccgcacag
atgcgtaaggagaaaataccgcatcaggcgaaattgtaaacgttaatattttgttaaaattcgcgttaaatattt
gttaaatcagctcatttttaaccaataggccgaaatcggcaaaatcccttataaatcaaagaatagaccgaga
tagggttgagtgttgttccagtttggaacaagagtccactattaaagaacgtggactccaacgtcaaagggcgaa
aaaccgtctatcagggcgatggcccactacgtgaaccatcccaaatcaagttttttgcggtcgaggtgccgta
aagctctaaatcggaaccctaaagggagcccccgatttagagcttgacggggaaagccggcgaacgtggcgagaa
aggaagggaagaaagcgaaaggagcgggcgctagggcgctggcaagtgtagcggtcacgctgcgcgtaaccacca
cacccgccgcgcttaatgcgccgctacagggcgcgtccattcgccattcaggctgcgcaactgttgggaagggcg
atcggtgcgggcctcttcgctattacgccagctggcgaaaggggatgtgctgcaaggcgattaagttgggtaac
gccagggttttcccagtcacgacgttgtaaaacgacggccagtgaattgtaatacgactcactatagggcgaatt
caaaaaccccctcaagacccgtttagaggccccaaggggttatgctagtgaattctgcagggtacccggggatcc
tctagagatccctcgacctcgagatccattgtgctgg
```

Nucleotide sequence of pGX6:   *FIG. 15.*

```
gaattcttggagttgggcaagctctgttgggtggatcatcgtgtgtcattagaaaaaaattctcggctagcaact
tttggagggattgtgtaaagtatgattgtacagtttcacaatacattggagagatttgtcggtacttgttggctc
agccagttgtggaagaggaatccaggcatagtgagttttgaaagttcttttaactttttaaactttttattaaaaat
tgttactccaggaatgagattgttggttggaaacggactccgtgctgaaatctggcaaccatttgtagatcgatt
ccgtgtcagaattggagaactttatggttcaactgaaggaacttcatctctcggtatgcatttttttttttcaaaa
gcacaagatcgatttaccttgaactataaaataagaaatatatcatgcaatttttgtaaaaatatatttaaaaaa
ttgagaagtttagccaaaaccttagatttttgcccgcttctgctcgtgttaaccgttctgtttcaacattaaatc
taatttctggccatttcagtgaacattgacggacatgtcggagcttgcggattcttgccaatatccccattaaca
aagaaaatgcatccggttcgattaattaaggttgatgatgtcactggagaagcaatccgaacttccgatggactt
tgcattgcatgtaatccaggagagtctggagcaatggtgtcgacgatcagaaaaataatccattattgcaattc
gagggatatctgaataagaaggaaacgaataaaaagattatcagagatgtcttcgcaaagggagatagttgcttt
ttgactggagatcttcttcattgggatcgtcttggttatgtatatttcaaggatcgtactggagatactttccgt
tggaagggagagaatgtgtcgactactgaagtcgaggcaattcttcatccaattactggattgccagcacaatgg
atctcgagggatcttccataccaccagttctgcgcctgcaggtcgcggccgcgactctctagacgcgtaagctt
actagcataacccttgggcctctaaacgggtcttgagggttttttgagcttctcgccctatagtgagtcgta
ttacagcttgagtattctatagtgtcacctaaatagcttggcgtaatcatggtcatagctgtttcctgtgtgaaa
ttgttatccgctcacaattccacacaacatacgagccggaagcataaagtgtaaagcctggggtgcctaatgagt
gagctaactcacattaattgcgttgcgctcactgcccgctttccagtcgggaaacctgtcgtgccagctgcatta
atgaatcggccaacgcgcggggagaggcggtttgcgtattgggcgctcttccgcttcctcgctcactgactcgct
gcgctcggtcgttcggctgcggcgagcggtatcagctcactcaaaggcggtaatacggttatccacagaatcagg
ggataacgcaggaaagaacatgtgagcaaaaggccagcaaaaggccaggaaccgtaaaaaggccgcgttgctggc
gtttttcgataggctccgcccccctgacgagcatcacaaaaatcgacgctcaagtcagaggtggcgaaacccgac
aggactataaagataccaggcgtttccccctggaagctccctcgtgcgctctcctgttccgaccctgccgcttac
cggatacctgtccgcctttctcccttcgggaagcgtggcgctttctcatagctcacgctgtaggtatctcagttc
ggtgtaggtcgttcgctccaagctgggctgtgtgcacgaaccccccgttcagcccgaccgctgcgccttatccgg
taactatcgtcttgagtccaacccggtaagacacgacttatcgccactggcagcagccactggtaacaggattag
cagagcgaggtatgtaggcggtgctacagagttcttgaagtggtggcctaactacggctacactagaaggacagt
atttggtatctgcgctctgctgaagccagttaccttcggaaaaagagttggtagctcttgatccggcaaacaaac
caccgctggtagcggtggtttttttgtttgcaagcagcagattacgcgcagaaaaaaggatctcaagaagatcc
tttgatcttttctacggggtctgacgctcagtggaacgaaaactcacgttaagggattttggtcatgagattatc
aaaaaggatcttcacctagatccttttaaattaaaaatgaagttttaaatcaatctaaagtatatatgagtaaac
ttggtctgacagttaccaatgcttaatcagtgaggcacctatctcagcgatctgtctatttcgttcatccatagt
tgcctgactccccgtcgtgtagataactacgatacgggagggcttaccatctggccccagtgctgcaatgatacc
gcgagacccacgctcaccggctccagatttatcagcaataaaccagccagccggaagggccgagcgcagaagtgg
tcctgcaactttatccgcctccatccagtctattaattgttgccgggaagctagagtaagtagttcgccagttaa
tagtttgcgcaacgttgttggcattgctacaggcatcgtggtgtcacgctcgtcgtttggtatggcttcattcag
ctccggttcccaacgatcaaggcgagttacatgatccccatgttgtgcaaaaaagcggttagctccttcggtcc
tccgatcgttgtcagaagtaagttggccgcagtgttatcactcatggttatggcagcactgcataattctcttac
tgtcatgccatccgtaagatgcttttctgtgactggtgagtactcaaccaagtcattctgagaataccgcgcccg
gcgaccgagttgctcttgcccggcgtcaatacgggataatagtgtatgcatacagcagaactttaaaagtgctcat
cattggaaaacgttcttcggggcgaaaactctcaaggatcttaccgctgttgagatccagttcgatgtaacccac
tcgtgcacccaactgatcttcagcatcttttactttcaccagcgtttctgggtgagcaaaaacaggaaggcaaaa
tgccgcaaaaaagggaataagggcgacacggaaatgttgaatactcatactcttcctttttcaatattattgaag
catttatcagggttattgtctcatgagcggatacatatttgaatgtatttagaaaaataaacaaataggggttcc
gcgcacatttccccgaaaagtgccacctgacgtctaagaaaccattattatcatgacattaacctataaaaatag
gcgtatcacgaggccctttcgtctcgcgcgtttcggtgatgacggtgaaaacctctgacacatgcagctcccgga
gacggtcacagcttgtctgtaagcggatgccgggagcagacaagcccgtcagggcgcgtcagcgggtgttggcgg
gtgtcggggctggcttaactatgcggcatcagagcagattgtactgagagtgcaccatatgcggtgtgaaatacc
gcacagatgcgtaaggagaaaataccgcatcaggcgaaattgtaaacgttaatattttgttaaaattcgcgttaa
atatttgttaaatcagctcattttttaaccaataggccgaaatcggcaaaatcccttataaatcaaagaatag
accgagatagggttgagtgttgttccagtttggaacaagagtccactattaaagaacgtggactccaacgtcaaag
ggcgaaaaccgtctatcagggcgatggcccactacgtgaaccatcacccaaatcaagttttttgcggtcgaggt
gccgtaaagctctaaatcggaaccctaagggagcccccgatttagagcttgacggggaaagccggcgaacgtgg
cgagaaggaagggaagaaagcgaaaggagcgggcgctagggcgctggcaagtgtagcggtcacgctgcgcgtaa
ccaccacccgccgcgcttaatgcgccgctacagggcgcgtccattcgccattcaggctgcgcaactgttggga
agggcgatcggtgcgggcctcttcgctattacgccagctggcgaaaggggatgtgctgcaaggcgattaagttg
ggtaacgccagggttttcccagtcacgacgttgtaaaacgacggccagtgaattgtaatacgactcactataggg
cgaattcaaaaaaccctcaagacccgtttagaggccccaaggggttatgctagtgaattctgcagggtacccgg
ggatcctctagagatccctcgacctcgagatccattgtgctgg
```

LIPID UPTAKE ASSAYS

RELATED APPLICATIONS

This application claims the benefit under 35 U.S.C. 119 of Great Britain application number GB 0012229.1, filed May 19, 2000.

FIELD OF THE INVENTION

The invention relates to the use of microscopic nematodes such as *C. elegans* in functional high throughput in vivo assays suitable for the detection of inhibitors or activators of intestinal lipid uptake. Compounds identified as modulators of intestinal lipid uptake using the assays of the invention may provide lead compounds for the development of pharmaceutical agents useful in the treatment of diseases of the human or animal (e.g. mammal) body, and in particular diseases and disorders of human and/or animal metabolism, fat handling and/or fat storage, such as obesity, impaired fat metabolism and other related diseases such as diabetes type II and cardiovascular diseases.

BACKGROUND OF THE INVENTION

When fat reaches the intestines in vertebrates, the pancreatic lipase hydrolyses the triglycerides into smaller components designated free fatty acids and monoglycerides (mainly 2-monoacylglycerols). Fatty acids are long-chain hydrocarbon molecules containing a carboxylic moiety at one end. The numbering of carbons in fatty acids begins with the carbon of the carboxylate group.

Metabolically, fatty acids are important energy substrates because of their high calorific content. In a typical diet of Western developed countries, approximately 30–40% of the dietary calories are derived from lipids, mainly in the form of di- and triglycerides. The linkage between excessive dietary lipid consumption and several common pathophysiologic disorders, including heart disease, obesity and diabetes and cancer, has been widely documented (Watts, et al., Am J Clin Nutr 64, 202–9 (1996); Storlien et al., Science 237, 885–8 (1987)).

There are three major roles in the body for the free fatty acids:

1) as the components of more complex membrane lipids.
2) as the major components of stored fat in the form of triacylglycerols.
3) Metabolism of fatty acids by β-oxidation is also the major source of ATP as energy for most organisms, especially for mammalian cardiac muscle.

Until recently it was considered that the adsorption of fatty acids into the body during digestion was through passive diffusion rather than the active transport process, as was known for carbohydrates and amino acids. Presently at least five plasma membrane proteins have been identified and proposed as candidates for fatty acid transporters thus far. These include, but are not restricted to:

Plasma Membrane Fatty Acid Binding Protein (FABPpm),
Fatty Acid Translocase (FAT)
Caveolin, a 22-kDa fatty acid binding protein
Renal 56-kb FABP
Fatty Acid Transport Protein (FATP)

An overview of these membrane proteins has been published by Yuen Hui and David A. Bernlohr, Bioscience 2, 222–231 (1997).

The expression of FATP is regulated by certain transcription factors, such as the "PPAR" (peroxysome proliferator activated receptor)-transcription factors the "RXR" (Retinoid X receptor)-transcription factors, and similar factors. Therefore, activators of these receptors, respectively fibrates or antidiabetic thiazolidinedione and retinoic acid, can increase FATP expression. One of the six known human FATPs, FATP4, has recently been shown to possess the functional characteristics (presence and absence is correlated with increase or decrease in fatty acid uptake) and cellular location (highly expressed in the microvilli of intestinal enterocytes) that would be required in a major intestinal fatty acid transport protein (Stahl A, et al. Mol Cell Biol 4,299–308 (1999)). It is highly probable that the expression and activity of the other transporter proteins is regulated too.

Nucleotide sequences encoding for and protein sequences of these fatty acid transporter proteins, both the human proteins and their *C. elegans* homologues, can be found in publicly accessible sequence databases, such as GenBank (accessible at the National Center for Biotechnology Information website, http://www.ncbi.nlm.nih.gov/PubMed/) and the *C. elegans* database of the Sanger Centre, UK (accessible at the Sanger Centre website, http://wormbase.sanger.ac.uk/). Some examples of sequences and designation numbers are:

| | |
|---|---|
| FATP: | *C. elegans* F25D1.9 and D1009.1 |
| | *H. sapiens* AF055899, |
| Caveolin: | *C. elegans* C56A3.7 and T13F2.8 |
| | *H. sapiens* NM_001233, NM_001753, and NM_001234 |
| FAT: | *C. elegans* Y49E10.20 and Y76A2B.6 |
| | *H. sapiens* P16671 |
| FABP: | *C. elegans* W02D3.7, W02D36.5, T22G5.2 and F40F4.2 |
| | *H. sapiens* NM_001445, NM_001443, and M10617 |

Although less well documented, proteins involved in the uptake of other lipids have been described in literature, and sequences of these proteins and genes have been published. For example, it has been shown that ABC transporters and more particularly the ABC transporter ABCB1 (ABC8) plays an important role in the regulation of Cholesterol and phospholipid transport (Klucken et al., Proc. Natl. Acad. Sci. USA, 2000, 97:817–822). Delivery of lipids, and more particularly sterols and cholesterol is done by the scavenger receptor-BI (Stangl et al., J. Biol. Chem., 1999, 274:32692–32698). Izzat et al. describe other putative targets to reduce the intestinal cholesterol uptake in the Journal of Pharmacology and Experimental Therapeutics 2000, 293:315–320. Such targets include bile acid transporters and HMG-CoA reductase. Cholesterol is taken up by the gut membrane without the involvement of a transporter. Compounds that interact stoichiometrically with the cholesterol in the intestinal lumen would also reduce cholesterol uptake. Other transporter proteins can be found in literature.

Controlling the uptake of lipids in the intestines would allow the treatment of obesity as well as the treatment of some related diseases such as diabetes mellitus, cardiovascular diseases such as arteriosclerosis, hypertension, stroke and certain forms of cancer. Enhancing lipid uptake in other tissues may also have specific therapeutic applications. For example, enhanced uptake of fatty acids by the skin will result in improved cosmetics.

SUMMARY OF THE INVENTION

The present inventors describe herein a functional assay to measure the uptake of lipids in vivo in a real intestine environment using small microscopic nematodes, such as *Caenorhabditis elegans*, as an animal model. Specific applications of this method are also described.

Therefore, in accordance with a first aspect of the invention there is provided a method of assaying lipid uptake in microscopic nematode worms which comprises:

incubating the said microscopic nematode worms in the presence of a probe molecule comprising a lipid moiety linked to a signal generating label; and determining the amount of probe molecule taken up by the said microscopic nematode worms by detecting a signal generated by the label part of the probe molecule.

In the assays of the invention, the nematode worms are incubated to a medium containing the probe molecule. Upon such incubation, the probe is taken up into the gastrointestinal tract of the nematode (e.g. by pharynx pumping), and in particular into the gut (lumen) of the nematode.

From the gut lumen, the probe may then pass from the gut lumen through the wall of the gastrointestinal tract (i.e. of the gut) into the body of the nematode, where it may concentrate in specific cells or tissues, such as the gut granules and/or other cells and tissues that store or handle lipids.

According to the invention, this passing of the probe molecule(s) from the gut lumen of the nematode into the body of the nematode is used as an in vivo model for lipid transport across biological membranes or barriers, not just in nematodes, but also in higher multicellular organisms, such as vertebrates, mammals and even humans. (In this respect, it should also be noted that the passing of the probe molecule(s) from the gut lumen of the nematode into the body of the nematode may not just be used as a model for lipid transport across the wall of the gastrointestinal tract, but generally as a model for lipid transport across any biological membrane and/or barrier, including epithelial cells/cell layers—such as the walls of blood vessels—and cell membranes.)

The invention is not particularly limited as to the mechanism or pathway via which said lipid transport may take place (i.e. both in nematode used in the assay of the invention as well as in the higher organism for which the nematode serves as an in vivo model) and may for instance include mechanisms such as active transport (which is preferred) and (passive) diffusion, or a combination thereof. In one embodiment, the invention may even be used to determine if, under the conditions of the assay (i.e. as used as a model), a probe or lipid is transported by an active transport mechanism or by a passive transport mechanism (e.g. by diffusion).

This may also depend on the specific type of lipid or probe involved (i.e. on the type of lipid moiety present in the probe), and—for the assay of the invention—on the specific worm strain used, on genetic factors influencing the worm strain used (such as gene suppression, e.g. as induced by RNAi methodology) and/or on the induction or suppression of specific pathways in the nematode(s) used, e.g. as a result of exposure of the worms to compounds that induce or suppress (the expression of) certain pathways involved in lipid transport and/or of specific genes and/or enzymes that are involved in such pathways (as further described below.)

As will be appreciated, to measure (active or passive) transport of a probe molecule from the gut lumen into the body of the nematode in vivo, it would in principle be necessary to measure, over a relevant period of time, either the amount and/or concentration of probe in the gut lumen (and/or any changes therein), the amount and/or concentration of probe in the body of the nematode (and/or any changes therein), or both. However, this would be very elaborate, would require examination of individual worms—e.g. using microscopy techniques—and even so would probably still not afford quantitative and/or statistically relevant results. Also, any such measurement would not be suitable for automation and/or for screening at medium to high throughput.

Thus, it is one of the general objects of the present invention to provide an assay for measuring lipid uptake/transport in vivo, which assay can serve as an in vivo model for lipid uptake/transport across biological membranes or barriers in (higher) multicellular animals, and which assay can be susceptible to—i.e. can be configured for—automation and/or to screening at medium to high throughput.

More specifically, it is an object of the invention to provide such an assay using nematode worms as a model organism.

One particular purpose of the invention is to provide such an assay which can be used for determining the influence on such lipid uptake/transport of small molecules, of induction or suppression of pathways involved in lipid uptake/transport (e.g. by prolonged exposure to inducing or suppressing factors), and/or of genetic factors such as mutations or RNAi-induced gene suppression.

In this way, the assay of the invention could be used to screen libraries of chemical compounds for small molecules and/or for (other) factors that can influence lipid uptake/transport across biological membranes/barrier, which small molecules or factors could then be used (as a starting point) in the development of compounds for use in compositions for increasing or decreasing lipid uptake/transport across biological membranes/barriers in multicellular organisms, including vertebrates such as mammals and humans, and more generally for influencing or altering fat and/or lipid handling or storage by such multicellular organisms, which can have relevance for a number of disease areas in animals and humans, including but not limited to obesity, diabetes and cardiovascular diseases (and in particular those relating to cholesterol handing and metabolism).

In addition to screening chemical libraries, the assay of the invention could also be used in drug development, e.g. in hits-to-leads chemistry or lead development, but also in genetic screens, gene discovery techniques, target validation techniques and/or other (functional) genomics techniques.

In a specific embodiment, the assays of the invention may also be used to measure/determine the uptake of specific components of food or food compositions (e.g. for human or animal use), such as fatty acids, fats, oils cholesterol-like compounds and/or other lipids (e.g. as defined below), as well as of compounds that are intended to replace fats, oils and/or lipids (for instance in food compositions for human consumption), and/or for additives—e.g. for food compositions—that are intended to lower cholesterol in the animal or person that consumes said composition. In this specific aspect of the invention, the assay may be used as a model for the uptake of such compounds from the gastrointestinal tract of a higher animal, such as an animal or human, e.g. to determine components which show increased or reduced uptake from the g.i. tract (i.e. compared to a reference). Thus, the assays of the invention may also be used in the development of components/additives for food, such as dietary compositions for human consumption, (specialized) nutritional compositions, and/or infant formula, or components for use therein.

The invention achieves the objects referred to above by providing the assay techniques described herein.

BRIEF DESCRIPTION OF THE DRAWINGS

FIG. 10(a) representation of plasmid pGN29, (b) representation of plasmid pGx5, (c) representation of plasmid pGX6.

FIG. 14 shows the complete nucleotide sequence of the plasmid pGX5 (SEQ ID NO:1).

FIG. 15 shows the complete nucleotide sequence of the plasmid pGX6 (SEQ ID NO:2).

DETAILED DESCRIPTION OF THE INVENTION

Figure 1:
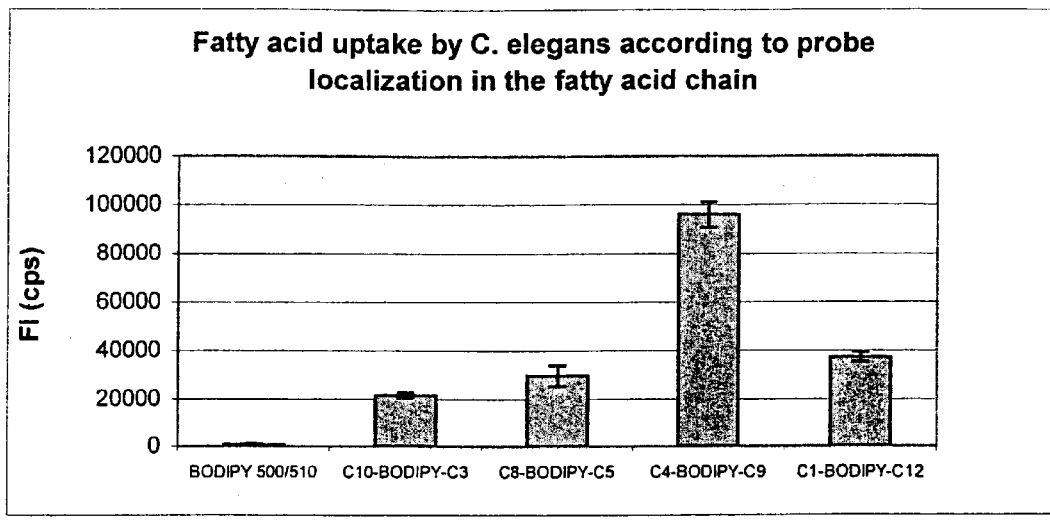
FIG. 1 is a graph to show the performance of a number of different BODIPY labelled fatty acid probes in a fatty acid uptake assay. Y axis is fluorescence intensity (FI, cps)

The invention relates to the use of microscopic nematodes such as C. elegans in functional high throughput in vivo assays suitable for the detection of inhibitors or activators of intestinal lipid uptake.

These techniques are inter alia based on the discovery that, under the assay conditions described herein, a signal generated by the entire body of a nematode worm (including the gut lumen), and in particular by a sample of nematode worms (as defined below), can serve as a (quantitative) measure of lipid transport/uptake by said nematode worm (s), i.e. from the gut (lumen) into the body of the nematode.

Thus, when the assay conditions described herein are used, there is no need to separately measure (the signal due to) the amount of probe in the gut lumen, and/or (the signal due to) the amount of probe in the body of the nematode, nor any changes therein.

Also, as according to the invention, a signal derived from the entire nematode worm (i.e. upon incubation with the probe as described herein), and in particular from a sample of nematode worms, is used as a quantitative signal for measuring lipid transport, the assay of the invention can be used with conventional techniques and equipment for handling (samples of) nematode worms and for measuring signals generated by (samples of) nematode worms, such as fluorescence techniques. This allows the assay of the invention to be automated and/or to be configured for screening at medium to high throughput, using well known (automated) techniques for handling and using nematode worms in medium to high throughput screening.

Even more surprising, it has been found that—under the assay conditions described herein—the signal generated by the (entire) sample of nematodes is even representative for lipid uptake when the worms are still in contact with a medium containing the probe molecule, i.e. such that the worms may still take up (additional) probe into their gastrointestinal tract (e.g. through pharynx pumping). [However, the latter is not required when carrying out the assays of the invention, as further described below].

Thus, in one particular preferred aspect, the invention relates to a method for determining the lipid uptake/transport of a probe molecule from the gut (lumen) of a nematode worm into the body of the nematode worm, said method comprising:

a) providing a sample of at least 15 nematode worms,
 b) contacting said sample of nematode worms with at least one probe molecule, said probe molecule containing at least one lipid moiety and at least one signal generating moiety, for a time of at least 15 minutes;
 c) subjecting the sample of worms to at least one detection technique, said detection technique being capable of detecting a signal generated by the probe molecule (or at least the signal generating part thereof).

Preferably, in this method, a sample of at least 20 worms is contacted with the probe for at least 20 minutes.

In one preferred embodiment, the probe is a quenched probe, as further described hereinbelow.

The sample of worms used is step a) preferably comprises between 20 and 500 worms, preferably between 30 and 200 worms, more preferably between 40 and 100 worms, such as about 50 worms (although the upper limits given here may not be critical).

It has also been found that the signal generated by the sample is not only representative for the amount of lipid(s) taken up by the (sample of) nematodes worms (with increased signal showing increased lipid uptake, and decreased signal showing decreased lipid uptake, e.g. both compared to a reference), but also increases in a linear fashion with the size of the sample (thus allowing, by choice of the size of the sample, the general level of signal strength to be regulated).

The worms present in the sample are preferably essentially the same, in that they belong to the same strain, in that they are essentially in the same stage of development (i.e. synchronized), in that they have been grown under the same conditions (e.g. in liquid or on plates), and/or in that they have been contacted with the same compounds or factors (e.g. for inducing certain pathways or enzymes involved therein). Preferably, either L4 worms or adult worms are used.

Each individual sample of worms is preferably present in an individual holder, container or compartment, such as a single agar plate or a single well of a multi-well plate (in which each well may contain a separate sample of worms).

The sample of worms is preferably kept in or on a suitable medium, such as in a liquid medium, in a viscous medium (e.g. a medium having a viscosity equal to or greater than M9 medium at the temperature of the assay, as determined by a suitable viscosity measurement technique such as an Ostwald or Brookfield viscosimeter or another suitable technique), a semi solid medium or a solid medium (such as agar). Such viscous media may—for example—essentially be as described in International application PCT/IB00/00575 ("Compound screening method"), published on 26-10-2000, and as described therein may for instance be obtained by adding a water-soluble polymer such as CMC to a liquid medium, in the amounts/concentrations as described therein.

Such a medium may further contain all factors and nutrients necessary for maintenance/survival of the worms, such as a suitable source of food, such as bacteria.

When the assays of the invention are carried out in multi-well plate format, the use of a liquid or viscous medium is usually preferred.

The invention also involves the use of a probe containing at least one lipid moiety and at least one signal generating moiety (as will be further described hereinbelow). The concentration of the probe in the medium is preferably between 1 micromolar and 500 micromolar, preferably between 2 micromolar and 100 micromolar, more preferably between 3 micromolar and 50 micromolar, and more preferably between 5 micromolar and 20 micromolar, such as about 10 micromolar (although the upper limits given here may not be critical).

It is also within the scope of the invention to contact the sample of nematodes with two or more different probes, as least one of which contains a lipid moiety. For instance, the sample of nematodes may be contacted with:

1) two or more probes each containing a different lipid moiety (e.g. to compare the uptake of these probes, e.g. relative to each other).
2) one probe that contains a lipid moiety (i.e. to measure lipid transport) and one that does not contain a lipid moiety (e.g. a probe designed/suitable for measuring pharynx pumping).

This embodiment may allow for both lipid uptake and pharynx pumping to be measured essentially at the same time (i.e. within the same sample of nematodes), for example to correlate (the rate of) pharynx pumping with (the rate of) lipid uptake/transport; to correct the amount/rate of lipid uptake measured for the amount/rate of pharynx pumping, and/or to ensure that, from one sample of worms to the next, the amount of pharynx pumping is essentially the same.

Suitable probes for measuring pharynx pumping (and suitable concentrations for such probes) are for instance described in International applications PCT/IB00/00575 (published on Oct. 26, 2000 as WO 00/63427) and PCT/IB00/00557 (published on Oct. 26, 2000 as WO 00/63425). [In this respect, it should be noted that, compared to techniques wherein (only) pharynx pumping is measured—such as described in these two applications—the present invention uses a probe that contains at least one lipid moiety, and is therefore (potentially) capable of passing from the gut lumen into the body of the nematode.]

3) one probe containing a lipid moiety (i.e. for measuring active transport) and a reference probe for measuring passive diffusion (such as BCECF).

In all these embodiments, the probes used will preferably contain at least one signal generating moiety. When two or more probes are used, they are preferably chosen such that they each generate a signal that can be detected separately from the signal generated by the other probe(s), allowing each probe to be measured individually. For instance, each individual probe may contain a signal-generating moiety that fluoresces at a separate wavelength.

In principle, as the nematode strain, any desired strain of nematode can be used, such as wildtype or N2.

In one embodiment, the nematode (strain) used may show constitutive pharyngeal pumping, at least under the conditions of the assay. Examples thereof are the so-called "high drinker" ("HD") strains, such as HD8. Such constitutive pumping strains may in particular be used when the assay of the invention is carried out in liquid or viscous medium (as opposed to on agar plates). Also, or alternatively, in order to induce/enhance pharynx pumping, the worms maybe kept/grown in the presence of a suitable source of food, such as bacteria.

In another embodiment, which may for instance be applied as part of a genetic screen, the nematode (strain) used has been obtained as a result of (random) mutagenesis, e.g. to determine the influence—if any—that the mutation(s) induced by said mutagenesis may have on lipid transport/uptake in the worm. In this way—e.g. by identifying mutants that have altered properties of lipid uptake/transport compared to the original strain, and then identifying the gene(s) that have been mutated in said strain—genes and/or mutations that may influence lipid transport/uptake may be identified, e.g. for target identification, target validation or other (functional) genomics purposes.

In another embodiment, a nematode (strain) is used which has altered properties of lipid (fat) handling, metabolism or storage compared to the wildtype nematode. For instance, these may be strains that have altered properties of entering into and/or being rescued from the dauer state (compared to the wildtype) such as the so-called daf-mutants, such as daf-2, daf-18 or daf-9.

Another type of mutants that may be used in the assays of the invention are the so-called ges mutants, such as ges-1.

In another embodiment, a nematode (strain) is used in which (one or more genes/enzymes of) one or more pathways relating to lipid uptake/transport have been induced or suppressed, e.g. as a result of gene suppression (e.g. using RNAi) and/or due to prolonged exposure to an inducing factor such as an inducing small compound. This may also take advantage of the fact that *C. elegans* has a relatively short life cycle, so that exposure to an inducing factor to over a relatively short period of time (e.g. hours) may already lead to an induction or suppression of such a pathway (optionally via induction or suppression of (the expression of) relevant transcription factors such as PPAR-transcription factors).

The temperature used in the assay is preferably between 5 and 50° C., more preferably between 10 and 30° C., and even more preferably between 15 and 30° C., e.g. about 20° C. or about 25° C.

The incubation time of the nematodes with the probe will depend upon factors such as the particular worm strain used, the concentration of the probe in the medium, and may also depend on the type of probe used.

In the invention, the incubation time is preferably such that:

(i) the probe molecule is taken up from the medium into the gastrointestinal tract of the nematode worm, and in particular into at least the gut (lumen) of the nematode worm;

(ii) (optionally, e.g. when the probe molecule is a quenched probe as further described below) the probe molecule is cleaved in the gastrointestinal tract of the nematode worm (e.g. by enzymatic or chemical cleavage), as further outlined below;

(iii) an amount of probe molecule (or at least one detectable part or moiety of the probe molecule, e.g. as obtained from cleavage of a quenched probe) is allowed to pass from the gut (lumen) through the wall of the gastrointestinal tract into (at least one part, cell or tissue of) the body of the nematode.

The incubation time with the probe is preferably such that the amount referred to under (iii) is such that it is representative for the amount of probe that has been taken up from the gut lumen into the body of the nematode, and even more preferably so that this amount is representative for the (level/amount of) lipid uptake/transport.

Even more so, the incubation time is such that (the level/strength/amount of) the resulting signal—i.e. as measured in step c) above—is representative for the uptake of the probe (or said at least one detectable part or moiety thereof) from the gut (lumen) of the nematode worm into (at least one part, cell or tissue of) the body of the nematode worm, which in turn is preferably representative for the amount of lipid uptake/transport.

Generally, the incubation time will be at least 15 minutes, preferably at least 20 minutes, more preferably at least 30 minutes, even more preferably at least 45 minutes, and may extend up to 6 hours or more. Usually, the incubation time will be about 1 hour.

Generally, in the invention, an increase of lipid uptake will lead to an increase in signal measured, whereas a decrease of lipid uptake will lead to a decrease in signal measured. Also, within the sample sizes mentioned above, the amount of signal measured may also increase with the size of the sample, e.g. in an essentially linear fashion.

The method of the invention is specifically adapted for assaying uptake of lipids through the gut of microscopic nematodes.

The preferred model organism for use in the method of the invention is the free living nematode *Caenorhabditis elegans* (*C. elegans*), which can be considered as the most well known multicellular organism. Its entire genome has been sequenced and the developmental stages has been studied and analyzed. The presence of a real intestine with microvilli and the transparency of the animal makes *C. elegans* an unique functional model to assess and measure lipid uptake in the gut.

Although *C. elegans* is the most preferred nematode for use in the method of the invention it will be appreciated that the method may also be carried out with other nematodes and in particular with other microscopic nematodes, preferably microscopic nematodes belonging to the genus Caenorhabditis. As used herein the term "microscopic" nematode encompasses nematodes of approximately the same size as *C. elegans*, being of the order 1 mm long in the adult stage. Microscopic nematodes of this approximate size are extremely well suited for use in mid- to high-throughput screening as they can easily be grown in the wells of a multi-well plate of the type generally used in the art to perform such screening.

The method of the invention may essentially be divided into two stages: (i) incubation of (the sample of) the nematode worms in the presence of a probe molecule, and (ii) determination of amount of probe molecule taken up by the (sample of) worms, as a measure of lipid uptake. Intermediate washing steps may be included between step (i) and step (ii), the purpose of these washing steps being to remove excess probe which has not been taken up by the worms.

The incubation step (i) may be performed on a solid nematode culture media, such as an agar plate or in liquid culture medium. Where the probe incubation is performed on solid culture media it is necessary to re-harvest the nematodes prior to the determination of probe uptake (step (ii)). If the probe incubation is performed in liquid culture the re-harvesting step is not necessary and the entire assay, including probe incubation, washing steps and uptake determination, can be performed in a single vessel, such as the wells of a microtiter plate. The determination step (ii) is in both cases preferably carried out in a microtiter plate to allow mid- to high-throughput determination using a microtiter plate reader.

Probe molecules suitable for use in the method of the invention generally comprise a lipid moiety linked (preferably via a covalent linkage) to a signal generating label portion. The lipid moiety is preferably a fatty acid, a steroid such as cholesterol, a phospholipid or a mono-, di- or triglyceride.

Preferably, the lipid moiety contains at least one C6 to C30, preferably C8 to C24, saturated, unsaturated or polyunsaturated fatty acid residue, optionally as part of a mono-, di- or triglyceride (residue, e.g. as part of a fat or oil residue), or as part of a phospholipid residue.

Alternatively, the lipid moiety contains at least one sterol/steroid residue such as cholesterol (i.e. a compound at least containing the four-membered ring skeleton present in cholesterol and other sterols/steroids).

The lipid moiety may be a naturally occurring lipid molecule or a synthetic structural analog of a naturally occurring lipid. The only requirement is that the lipid moiety should be a substrate for a pathway of lipid uptake via the gut of the nematode.

Other lipids that may be used (i.e. tested in the model of the invention and/or incorporated) will be clear to the skilled person, and the invention is not particularly limited as to the specific structure of the lipid (moiety), as long as at least one fatty acid residue or sterol/type residue is present.

The signal generating label portion of the probe may be essentially any type of label which is capable of generating a signal which is detectable through the body of the nematode. These include fluorescent, luminescent and coloured labels, fluorescent labels being the most preferred. The label portion should ideally be chosen such that its presence in the probe molecule does not unduly interfere with the pathway of lipid uptake.

Preferred types of probe molecules which may be used in accordance with the invention include lipids labelled with BODIPY, diphenylhexatriene (DPH), NBD, pyrene or perylene. Other types of fluorescent labels such as fluorescein or Texas-red may also be used.

A range of labelled lipids which may be used as probe molecules in the method of the invention are available commercially, for example from Molecular Probes, Eugene, Oreg., USA.

In one particular embodiment of the invention the probe molecule may comprise a lipid moiety, a fluorescent label portion and further a quencher portion which is a molecule adapted to quench fluorescence emitted from the fluorescent label portion of the probe. The quencher portion should preferably be linked to the remainder of probe molecule via a (preferably covalent) bond which is cleavable or hydrolyzable by an enzyme present in the intestinal lumen of the nematode, such as, for example, an esterase or a protease. A preferred label/quencher combination is BODIPY/DNP, as discussed in the accompanying Example 8.

The nature of the probe, in particular the nature of the lipid moiety, will determine the lipid selectivity of any given lipid uptake assay. Thus, assays using probes comprising a labelled fatty acid will generally be selective for fatty acid uptake, whereas assays using probes comprising labelled cholesterol will generally be selective for cholesterol uptake. In addition, probes based on labelled fatty acids may exhibit a further level of specificity, e.g. specificity for saturated vs unsaturated fatty acids. For any given probe, the lipid selectivity of the lipid uptake assay can be determined using a competition experiment, such as that described in Example 4.

For any given application of the method of the invention the optimum concentration of probe and optimum length of incubation of the nematodes with the probe may be determined by routine experiment, as mentioned above and as further illustrated in the accompanying Examples. It has also been observed that the rate of lipid uptake may vary depending on the life cycle of the nematode, with different rates of uptake being observed in worms at different growth stages. Furthermore, the pattern of uptake may vary from strain-to-strain. Thus, for any given nematode strain (e.g. wild-type, specific mutant or transgenic) at any given stage of the life cycle the optimum probe concentration and incubation time should be determined empirically, as would be a matter of routine to one of ordinary skill in the art.

The lipid uptake assay may be performed using wild-type nematodes and also non-wild type worms, for example specific mutant, transgenic or 'humanized' strains. The mutant worms may carry a mutation in a single gene or in two or more different genes. The transgenic strains can be strains expressing a transgene in the whole organism, or in a part of the organism, in a single tissue, in a sub-set of cell types, in a single cell type or even in one cell of the organism. The transgenic strains may further have a mutant genetic background. Humanized worms are particularly useful for the identification of compounds with potential therapeutic activity in the human pharmaceutical field as they can be used to perform screens which are specifically directed at human target proteins but which have all the advantages of the nematode biology and ease of manipulation.

Standard methods for culturing nematodes are described in Methods in Cell Biology Vol. 48, 1995, ed. by Epstein and Shakes, Academic Press. Standard methods are known for creating mutant worms with mutations in selected *C. elegans* genes, for example see J. Sutton and J. Hodgkin in "The Nematode *Caenorhabditis elegans*", Ed. by William B. Wood and the Community of *C. elegans* Researchers CSHL, 1988 594–595; Zwaal et al, "Target—Selected Gene Inactivation in *Caenorhabditis elegans* by using a Frozen Transposon Insertion Mutant Bank" 1993, Proc. Natl. Acad. Sci. USA 90 pp 7431–7435; Fire et al, Potent and Specific Genetic Interference by Double-Stranded RNA in *C. elegans* 1998, Nature 391, 860–811. A population of worms can be subjected to random mutagenesis by using EMS, TMP-UV or radiation (Methods in Cell Biology, Vol 48, ibid). Several selection rounds of PCR could then be performed to select a mutant worm with a deletion in a desired gene. In addition, a range of specific *C. elegans* mutants are available from the *C. elegans* mutant collection at the *C. elegans* Genetic Center, University of Minnesota, St Paul, Minn.

The nematodes may be subjected to further manipulations prior to the determination of lipid uptake. For example, expression of a target gene in the nematodes may be inhibited by RNAi technology (Fire et al., Nature 391:801–811 (1998); Timmons and Fire, Nature 395:854 (1998), Plaetinck et al., WO 00/01846). The nematodes may also be incubated in the presence of a chemical compound prior to determination of lipid uptake. This may be a compound having a known effect on lipid uptake (e.g. an inhibitor of a particular uptake pathway) or a compound having an unknown effect on lipid uptake.

The lipid uptake assay method of the invention essentially provides an assay read-out for lipid uptake in nematode worms which is of broad and general application. A number of specific applications of the lipid uptake assay methodology will be described below.

In one application, the lipid uptake assay methodology may be used to perform screens to identify compounds which are inhibitors or enhancers of lipid uptake. These compound screens essentially comprise exposing microscopic nematode worms to a test compound and then determining the effect of exposure to the compound on lipid uptake using a lipid uptake assay according to the invention, as described above.

Accordingly, the invention provides a method of identifying a compound as an inhibitor or an enhancer of lipid uptake using microscopic nematode worms, the method comprising:

incubating the said microscopic nematode worms in the presence of the said compound;

adding a probe molecule comprising a lipid moiety linked to a signal generating label and further incubating the microscopic nematode worms in the presence of the compound and the probe; and determining the amount of probe molecule taken up by the said microscopic nematode worms by detecting a signal generated from the label part of the probe molecule.

Although it is possible to perform the step of exposing the nematode to the compound and the incubation with the probe in the presence of the compound on solid media, such as an agar plate, the compound screening method of the invention is preferably carried out entirely in multi-well assay plates, making it suitable for use in mid-to-high throughput screening. The multi-well plates will preferably have 96 wells, but the invention is also applicable to multi-well plates with another number of wells, which include but is not restricted to plates with 6, 12, 24, 384, 864 or 1536 wells. The terms "multi-well plate" and "microtiter plate" are used interchangeably throughout.

Typically, compound screening assays involve running a plurality of assay mixtures in parallel with different concentrations of the compound under test. Typically, one of these concentrations serves as a negative control, i.e. zero concentration of test substance. Changes in lipid probe uptake resulting from exposure to the compound may then be evaluated in comparison to the negative control.

The compound screening method allows the rapid discovery of inhibitors and enhancers of the lipid uptake and transport, regardless of the target. Compounds identified using the assay may be lead compounds for the development of pharmaceutical agents which modulate lipid uptake.

The compound screening method is preferably carried out using the microscopic nematodes *C. elegans* or *C. briggsae*, *C. elegans* being the most preferred. It will, however, be appreciated that other microscopic nematode species could be used, as discussed above.

Due to the physical properties of lipids, and of the probes used to select for the uptake of lipids, it is difficult develop a high throughput screen to select for compounds that alter the uptake of lipids using classical cell culture techniques. It is further evident that other animal models such as mouse models would not be useful in the development of an appropriate high throughput screen. The use of nematodes and more particularly microscopic nematodes such as *C. elegans* and *C. briggsae* overcomes most, if not all, of these restrictions.

Tissue culture based methods to select for compounds that alter the lipid uptake have the further disadvantage that the screen is linked to a particular gene or gene product. In most if not all cases, a gene encoding for a protein involved in lipid uptake needs to be introduced and the protein needs to be expressed in the target cells. Once this is achieved, a specific screen to select for compounds that alter the uptake of lipids by affecting the introduced and expressed target gene can be developed. Thus, tissue culture methodology allows screening for compounds that act on the introduced gene, and expressed protein, but does not allow screening on the other components of complex mechanisms, such as the pathways of lipid uptake.

The use of microscopic nematodes such as *C. elegans* counters this problem. *C. elegans* is a multicellular organism that has all the ability for lipid uptake. Hence, no genes need to be introduced, or proteins need to be expressed in this organism to develop a suitable screen. The screening method described herein results in the isolation of compounds that alter the lipid uptake, independently of the target. In other words, the screen in *C. elegans* as developed by the inventors to select for compounds that alter the uptake of lipids may be target independent. In addition, the same methodology can be adapted to perform specific screens which target a specified gene or protein.

The ability to perform both target-independent and specific screens is a second major advantage of the use of *C. elegans* in screening for compounds that alter the uptake of lipids. As lipid uptake is considered to be a complex system involving several proteins and regulatory systems, it can be foreseen that only a minor number of the involved genes and proteins have been isolated and described in literature. The *C. elegans* screen described herein allows screening for compounds that affect previously unidentified components of the lipid uptake system, and also allows specific screening for compounds that affect well known components of the lipid uptake pathway.

Another advantage of *C. elegans* is that it is transparent (allowing the use of fluorescent probes or other probes that generate an optical signal, e.g. within the body of the nematode), that its genome is well characterised, and that it is of small size, allowing it to be used in multi-well plate format.

The method described by the inventors further allows selective screening for compounds that alter the activity of enzymes that are directly involved in the lipid uptake and compounds that alter the activity of activators and regulators. For example, in the uptake of fatty acids, at least the FABP, FAT, Caveolin, FATP enzymes are directly involved, while the PPAR and RXR enzymes are regulators in the fatty acid uptake pathway. Compounds which alter the activity of a lipid uptake protein or a direct activator or regulator of the activity of such transporter protein are expected to exert their effects on a short time scale of approximately two hours or less. In contrast, compounds which alter the activity of a regulator protein, being a regulator of the lipid uptake enzyme expression or being a transcription factor, or being any other type of regulatory enzyme, will exert their effects on a more prolonged time scale, ranging from three to more than sixteen hours. So by selecting the time range of the measurements in the method of the invention, it is possible to make a first selection on the diversity of targets that are altered by the compounds isolated.

The target selectivity of the compound screening assay may also be altered by changing the genetic background of the nematodes used to perform the assay. Thus, wild-type nematodes may be used to perform compound screens which are target-independent, whereas specific mutant, transgenic or mutant/transgenic strains may be used to perform target-specific screens. The use of specific humanized strains allows screening for compounds which act on specific components of human lipid uptake pathways.

The 'compounds' to be tested in the method of the invention may be is any foreign molecules not usually present in the worm or to which the worm would not normally be exposed during its life cycle. For example, the compound may be a compound listed in a pharmacopoeia with known pharmacological activity but unknown activity in lipid uptake pathways. Alternatively, the compound may be a known molecule with no known biological activity or completely new molecules or libraries of molecules such as might be generated by combinatorial chemistry. Compounds which are DNA, RNA, PNA, polypeptides or proteins are not excluded.

The compounds may be tested at any suitable concentration or range of concentrations (e.g. to establish a dose response curve). For example, suitable concentrations may be in the range of between 0.001 and 10,000 micromolar, preferably between 0.01 and 1000 micromolar, in particular between 0.05 and 500 micromolar, although the invention is not limited thereto.

It is also within the scope of the invention to expose the (sample of nematodes) to two or more compounds—at essentially the same time or sequentially (e.g. with an intermediate washing step)—for example to determine whether the two compounds have an influence on lipid uptake which is the same or different from both the compounds separately (e.g. to provide a synergistic effect or an inhibitory or competitive effect).

Suitable contact times of the compound and the (sample of) nematodes may be between 10 seconds and 48 hours, preferably between 1 minute and 36 hours, and may for instance be between 30 minutes and 24 hours. For instance, incubation of about 1 hr to overnight (e.g. about 16 hours) may be used.

The probe may be used at any suitable concentration, depending on factors such as the specific probe used, the size of the sample, the rate of pharynx pumping of the nematodes under the assay conditions, etc. For example, suitable concentrations of probe may be in the range of between 0.001 and 10,000 micromolar, preferably between 0.01 and 1000 micromolar, in particular between 0.05 and 500 micromolar, with between 1 and 200 micromolar, in particular between 10 and 100 micromolar being particularly preferred (although the invention is not limited thereto).

The (sample of nematodes) may be incubated with the compound(s) and the probe at essentially the same time or sequentially (e.g. with an intermediate washing step), with the latter usually being preferred.

The signal generated by the (signal generating part of) the probe may be measured in any suitable way, such as optical measurement (e.g. measurement of fluorescence and/or of another emitted or absorbed wavelength). The particular wavelength used will depend on the (signal generating part of) the probe used, as will be clear to the skilled person, and may for instance be within the visible, UV or IR spectrum. For example, automated plate readers for measuring fluorescence are known in the art and may be used in the present invention.

In a further application the lipid uptake methodology can be used to identify the molecular targets of compounds which alter lipid uptake in the basic compound screening method of the invention using the powerful genetic tools of microscopic nematodes such as *C. elegans*.

Accordingly, the invention provides a method of identifying components of the lipid uptake pathway on which a compound previously identified as an inhibitor or an enhancer of lipid uptake in microscopic nematode worms acts, which method comprises the steps of:

subjecting a population of microscopic nematode worms to random mutagenesis;

allowing mutagenized F1 nematode worms to generate F2 offspring;

identifying a suppressor mutant F2 nematode worm in which the effect of the said compound on lipid uptake is suppressed using the lipid uptake assay method according to the invention; and identifying the gene or genes which are mutated in the said mutant F2 nematode worm.

This application of the invention is, in effect, a classical genetic suppressor screen and is preferably carried out using the microscopic nematode *C. elegans*. In a suppressor screen the aim is to identify a mutation which suppresses the phenotype generated by exposure of the worm to a chemical compound. Therefore, to identify a suppressor mutant for a compound which is an inhibitor of lipid uptake one effectively looks for a 'resistance mutant' in which lipid uptake is no longer inhibited by addition of the compound. In order to identify a suppressor mutant for a compound which is an enhancer of lipid uptake one looks for a mutant in which addition of the compound causes no enhancement of lipid uptake.

Suppressor mutants can be generated quickly using standard mutagenesis techniques, identified using standard suppressor genetics and the target gene or genes mutated in the suppressor mutant can be isolated quite easily (see Methods in Cell Biology, vol. 48, 1995, "*Caenorhabditis elegans*: Modern biological analysis of an organism" Eds. H. F. Epstein and D. C. Shakes, Academic Press).

In a preferred embodiment, all steps of the suppressor screening method are carried out in microtiter plates, in which case the method comprises the steps of:

subjecting a population of microscopic nematode worms to random mutagenesis;

dispensing one mutagenized F1 nematode worm into each of the wells of a multi-well assay plate;

allowing the F1 nematode worms to generate F2 offspring;

incubating the F2 nematode worms in the presence of the compound;

adding a probe molecule comprising a lipid moiety linked to a signal generating label and further incubating the microscopic nematode worms in the presence of the compound and the probe;

determining the amount of probe molecule taken up by the said microscopic nematode worms by detecting a signal generated from the label part of the probe molecule and thereby identifying suppressor mutants in which the effect of the compound on lipid uptake is suppressed; and identifying the gene or genes which are mutated in the said mutant F2 nematode worm.

In a still further application, the lipid uptake methodology provided by the invention allows the isolation of new proteins and genes involved in the uptake of lipids. Using the method of the invention it is possible to identify and isolate mutant worm strains that have a reduced lipid uptake. The mutations present in such mutant strains may be in genes that are directly involved in lipid uptake, or involved in the regulation of lipid uptake. Using standard *C. elegans* genetics, the new gene and protein involved in lipid uptake which is mutated in a given mutant strain can be isolated.

Accordingly, the invention provides a method of isolating novel genes and proteins involved in pathways of lipid uptake in a microscopic nematode worm, which comprises:

subjecting a population of microscopic nematode worms to random mutagenesis;

identifying a mutant worm which exhibits altered lipid uptake as compared to wild-type using the lipid uptake assay described herein; and isolating the gene or genes which are mutated in the said mutant worm.

This application of the lipid uptake assay is again preferably carried out using *C. elegans*.

For comparison purposes in the context of this application, wild type *C. elegans* are taken to be the N2 Bristol strain which is well known to workers in the *C. elegans* field and has been extremely well characterized (see Methods in Cell Biology, Volume 48, Caenorhabditis elegans: Modern biological analysis of an organism, ed. by Henry F. Epstein and Diane C. Shakes, 1995 Academic Press; The nematode *Caenorhabditis elegans*, ed. by William Wood and the community of *C. elegans* researchers., 1988, Cold Spring Harbor Laboratory Press; *C. elegans* II, ed. by Donald L. Riddle, Thomas Blumenthal, Barbara J. Meyer and James R. Priess, 1997, Cold Spring Harbor Laboratory Press). The N2 strain can be obtained from CGC, University of Minnesota, USA.

In a further aspect of the present invention, there are provided novel compounds which are particularly suitable for use as probe molecules in the assays previously described. These probes generally comprise:

1. at least one signal generating moiety, 2. at least one lipid residue (as defined above), and 3. at least one enzyme cleavable and/or enzyme hydrolysable functional group, in which the at least one enzyme cleavable and/or enzyme hydrolysable functional group is preferably such that—in the period of time used for performing the assay—it is removed (i.e. by cleavage or hydrolysis) under the conditions prevalent in the gastrointestinal tract on the nematode (but—in the period of time used for performing the assay—it is essentially not removed under the conditions prevalent in the medium used);

and wherein the probe and the at least one enzyme cleavable and/or enzyme hydrolysable functional group are further such that, when the at least one enzyme cleavable and/or enzyme hydrolyzable group is removed (i.e. in the gastrointestinal tract of the nematode) the probe molecule (e.g. the signal generating part thereof) provides a signal that is different from the signal provided when the at least one enzyme cleavable and/or enzyme hydrolysable group is present.

Preferably, the probe and the at least one enzyme cleavable and/or enzyme hydrolysable functional group are such that, when the at least one enzyme cleavable and/or enzyme hydrolysable group is removed (i.e. in the gastrointestinal tract of the nematode) the probe molecule (e.g. the signal generating part thereof) provides a (detectable) signal (e.g. fluorescence or another optical signal), whereas when the at least one enzyme cleavable and/or enzyme hydrolyzable group is present, the probe provides essentially no such signal.

The invention also relates to the use of such a probe (also referred to herein as a "quenched probe") in an assay involving the use of at least one nematode worm (e.g. as a model organism), and in particular in such an assay for determining/measuring at least one metabolic process of the nematode worm, such as lipid uptake, transport or handling.

Accordingly, in a preferred embodiment, the present invention provides a compound of Formula I:

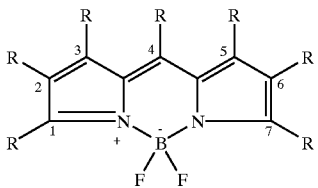

Formula I wherein:
one of the R groups (R') is —A—X—Q, wherein A is a saturated or unsaturated linear $C_{3-21}$ hydrocarbon chain, X is an enzyme cleavable or enzyme hydrolysable functional group, and Q is a quencher for the 4,4-difluoro-4-bora-3a,4a-diaza-s-indacene (BODIPY®) portion of the compound;

one of the R groups (R") is selected from the group consisting of H, $C_1$–$C_6$alkyl, $C_2$–$C_6$alkenyl, $C_2$–$C_6$alkynyl, aryl$C_1$–$C_6$alkyl, aryl$C_2$–$C_6$alkenyl, aryl$C_2$–$C_6$alkynyl, aryl, $C_1$–$C_6$alkoxyaryl, heteroaryl and saturated or unsaturated linear $C_3$–$C_{21}$ hydrocarbons;

the remaining R groups (R''') are each independently selected from the group consisting of H, $C_1$–$C_6$alkyl, $C_2$–$C_6$alkenyl, $C_2$–$C_6$alkynyl, aryl$C_1$–$C_6$alkyl, aryl$C_2$–$C_6$alkenyl, aryl$C_2$–$C_6$alkynyl, aryl, $C_1$–$C_6$alkoxyaryl and heteroaryl.

In the context of the present invention, the term "unsaturated", when used to qualify a particular functional group, means that said group contains one or more carbon-carbon double bonds and/or one or more carbon-carbon triple bonds.

In the context of the present invention, the term "enzyme cleavable", when used to qualify a particular functional group, means that said group may be decomposed by the action of a natural or synthetic enzyme.

In the context of the present invention, the term "enzyme hydrolyzable", when used to qualify a particular functional group, means that said group may be decomposed by the action of a natural or synthetic enzyme in the presence of water. Preferred enzyme hydrolyzable functional groups are ester and amide groups.

In the context of the present invention, the term "quencher" means any functional group capable of at least partially quenching the fluorescence of the BODIPY portion of the compound.

In the context of the present invention, the term "alkyl" means a linear or branched saturated hydrocarbon chain comprising the specified number of carbon atoms. A preferred alkyl group is methyl, ethyl, (n- or iso-) butyl, (n- or iso-) propyl, (linear or branched) pentyl or (linear or branched) hexyl.

In the context of the present invention, the term "alkenyl" means a linear or branched hydrocarbon chain comprising the specified number of carbon atoms and one or more carbon-carbon double bonds.

In the context of the present invention, the term "alkynyl" means a linear or branched hydrocarbon chain comprising the specified number of carbon atoms and one or more carbon-carbon triple bonds.

In the context of the present invention, the term "aryl" means phenyl or naphthyl.

In the context of the present invention, the term "heteroaryl" means a five- or six-membered aromatic ring comprising from one to three heteroatoms in the ring, said heteroatoms being each independently selected from N, O and S. Preferred heteroaryl groups include pyrrolyl, furanyl and thiophenyl, pyrazolyl, imidazolyl or pyridyl.

In the context of the present invention, the term "alkoxy" means a linear or branched saturated hydrocarbon chain comprising the specified number of carbon atoms linked to the substituted moiety via an oxygen atom. A preferred alkoxy group is methoxy, ethoxy, (n- or iso-) butyloxy, (n- or iso-) propyloxy, (linear or branched) pentyloxy, or (linear or branched) hexyloxy.

In a preferred embodiment at least any two R groups=H.

In another preferred embodiment at least any three R groups=H.

In another preferred embodiment at least any four R groups=H.

In another preferred embodiment at least any five R groups=H.

In a preferred embodiment, A is a saturated or unsaturated linear $C_6$–$C_{10}$ hydrocarbon chain. More preferably, A is a saturated linear $C_6$–$C_{10}$ hydrocarbon chain. Most preferably —A— is —$(CH_2)_8$—.

In a preferred embodiment, —X— is selected from —CO—O—, —O—CO—, —NH—CO— and —CO—NH—. Most preferably —X— is —CO—O—.

Q may be any moiety which acts as a quencher for the 4,4-difluoro-4-bora-3a,4a-diaza-s-indacene (BODIPY®) fluorophore portion of the compound. Suitable quencher groups include the 2,4-dinitrophenyl, functional groups.

Preferably, Q comprises a 2,4-dinitrophenyl functional group. More preferably Q is a group of Formula II

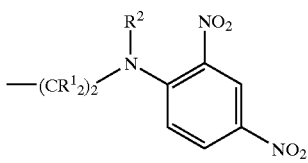

Formula II wherein each $R^1$ is independently selected from H, $CH_3$ and $CH_2CH_3$, with the proviso that at least two $R^1$ groups are H; and $R^2$ is selected from H, $CH_3$ and $CH_2CH_3$, preferably H. Most preferably Q is a group of Formula II wherein each $R^1$ is H and $R^2$ is H.

In a preferred embodiment the group R' is located at the 7-position as those positions are numbered in Formula I above.

In another preferred embodiment the group R' is located at the 4-position as those positions are numbered in Formula I above.

In a preferred embodiment R" is not H. That is to say, R" is preferably selected from the group consisting of $C_1$–$C_6$alkyl, $C_2$–$C_6$alkenyl, $C_2$–$C_6$alkynyl, aryl$C_1$–$C_6$alkyl, aryl$C_2$–$C_6$alkenyl, aryl$C_2$–$C_6$alkynyl, aryl, $C_1$–$C_6$alkoxyaryl, heteroaryl and saturated or unsaturated linear $C_3$–$C_{21}$ hydrocarbons. More preferably, R" is selected from the group consisting of $C_1$–$C_6$alkyl (in particular methyl), phenyl$C_2$–$C_6$alkenyl (in particular Ph-(CH=CH)$_m$— wherein m=1 or 2), phenyl, $C_{1-6}$alkoxyphenyl (in particular methoxyphenyl), heteroaryl (in particular thiophen-2-yl or pyrrol-2-yl) and saturated or unsaturated linear $C_3$–$C_{10}$ hydrocarbons. Most preferably R" is selected from saturated or unsaturated linear $C_3$–$C_6$ hydrocarbons.

When R" is not H, it is preferably located at the 1-, 3-, 5- or 7-position as those positions are numbered in Formula I above. More preferably, when R" is not H, it is located at the 1-position as those positions are numbered in Formula I above.

When R" is not H, and is located at the 1-position as those positions are numbered in Formula I above, any remaining R groups (R''') which are not H are preferably located at the 3- and/or 5- and/or 7-position(s) as those positions are numbered in Formula I above. In these situations, the remaining R groups (R''') which are not H are preferably selected from $C_1$–$C_6$alkyl (in particular methyl) and phenyl.

Particularly preferred compounds of the present invention are those of Formula I wherein:
one of the R groups (R') is located at the 4-, or 7-position as those positions are numbered in Formula I and is —A—X—Q, wherein A is a saturated or unsaturated linear $C_3$–$C_{21}$ hydrocarbon chain, X is selected from —CO—O— and —CO—NH—, and Q is a group of Formula II wherein each $R^1$ is independently selected from H, $CH_3$ and $CH_2CH_3$, with the proviso that at least two $R^1$ groups are H and $R^2$ is H;

one of the R groups (R") is located at the 1-position as those positions are numbered in Formula I and is selected from the group consisting of $C_1$–$C_6$alkyl, $C_1$–$C_6$alkenyl, $C_1$–$C_6$alkynyl, phenyl$C_1$–$C_6$alkenyl, phenyl, $C_1$–$C_6$alkoxyphenyl, heteroaryl and saturated or unsaturated linear $C_3$–$C_{21}$ hydrocarbons;

the remaining R groups (R''') are each independently selected from the group consisting of H, $C_1$–$C_6$alkyl, phenyl$C_1$–$C_6$alkenyl, phenyl, $C_1$–$C_6$alkoxyphenyl and heteroaryl and, if not H, are located at the 3 and/or 5-position(s) as those positions are numbered in Formula I.

Further preferred compounds of the present invention are those of Formula I wherein:
one of the R groups (R') is located at the 4- or 7-position as those positions are numbered in Formula I and is —A—X—Q, wherein A is a saturated or unsaturated linear $C_6$–$C_{10}$ hydrocarbon chain, X is —CO—O—, and Q is a group of Formula II wherein each $R^1$ is independently selected from H, $CH_3$ and $CH_2CH_3$, with the proviso that at least two $R^1$ groups are H and $R^2$ is H;

one of the R groups (R") is located at the 1-position as those positions are numbered in Formula I and is selected from the group consisting of saturated or unsaturated linear $C_3$–$C_6$ hydrocarbons; and the remaining R groups (R''') are all H.

A particularly preferred compound of the present invention is:

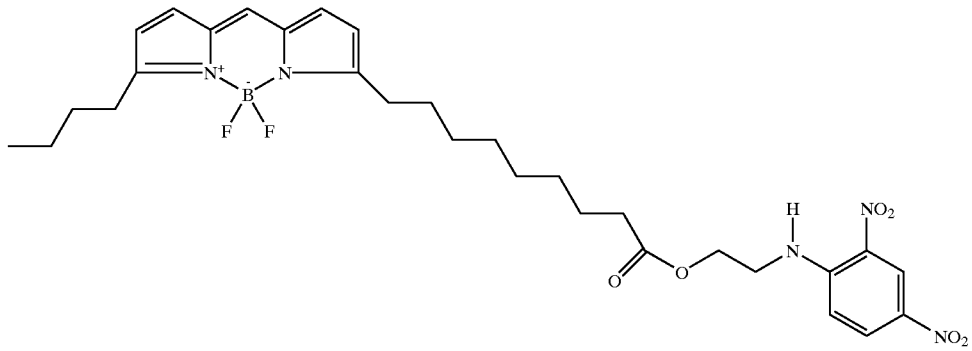

A general synthetic scheme for the synthesis of compounds of the present invention or intermediates thereof is set out in scheme 1 below:

Scheme 1

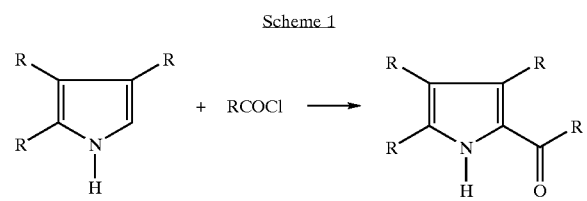

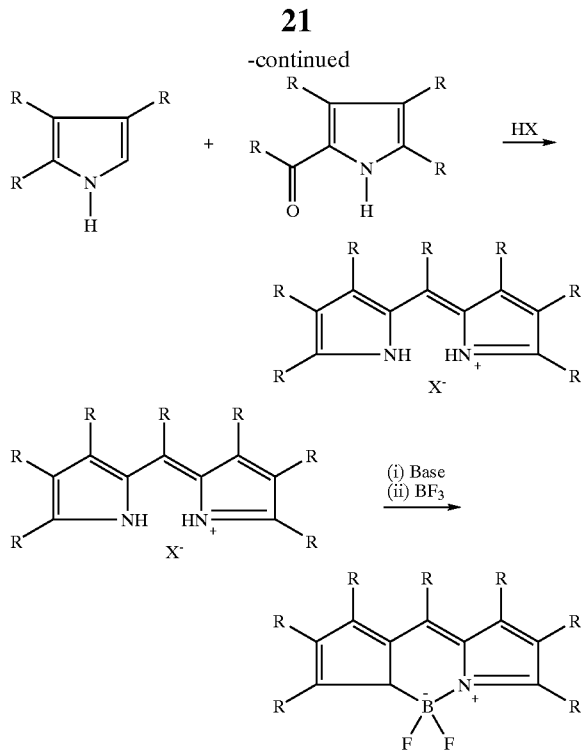

Note that where a symmetrical compound is desired the first two steps may be carried out simultaneously by the addition of two equivalents of the substituted pyrrole.

Introduction of the desired R group at the 4-position in the final product can be effected by selection of the corresponding substituted acyl chloride. Suitably substituted acid chlorides are either commercially available or may be readily synthesized by techniques well known to those skilled in the art (see for example page 1146 of Advanced Organic Chemistry, 3rd Edition, Jerry March, published by John Wiley & Sons).

Substitution of the pyrrole moieties may be effected either before or after formation of the BODIPY® moiety, depending upon the choice of substituent(s). Where substitution is effected before formation of the BODIPY® moiety, suitably substituted pyrroles are either commercially available or may be readily synthesised by techniques well known to those skilled in the art (see for example the website of Molecular Probes, the parts relating to the BODIPY® dyes (on the date of filing of this application: http://www.probes.com/handbook/sections/0103.html). Where substitution is effected after formation of the BODIPY® moiety further details on the synthesis of a wide range of compounds which comprise a BODIPY® portion which may be useful as intermediates in the synthesis of compounds of the present invention are described in U.S. Pat. Nos. 4,774,339 and 5,274,113.

Suitable intermediates which comprise a BODIPY® portion and which are particularly useful in the synthesis of compounds of the present invention are also commercially available from Molecular Probes, Inc. See for example Chapter 13 of the Handbook of Fluorescent Probes and Research Chemicals (sixth edition) by Richard P. Haughland.

Where the quencher group Q is not already incorporated into the molecule during synthesis according to scheme 1 above, such groups may be readily introduced into intermediate BODIPY® compounds so as to provide the necessary —A—X—Q group by synthetic procedures well known to those skilled in the art. For example, where the precursor to the group R=is —A—CO$_2$H, group Q may be added by means of esterification (using the alcohol Q—OH) or amidation (using the amine Q—NH$_2$) to provide the group —A—COO—Q or —A—CONH—Q.

The invention will be further understood with reference to the following non-limiting experimental examples.

EXAMPLES

General Methodology

1) Material and Methods

*C. elegans* strain HD8 (bg46 or hdr(bg46)) which exhibits constitutive pharyngeal pumping was deposited on 9 Feb. 2000 in accordance with the provisions of the Budapest Treaty on the International Recognition of the Deposit of Microorganisms in the Belgian Coordinated Collections of Microorganisms-BCCM LMBP- Collection, Universiteit Gent, K. L. Ledeganckstraat 35, B-9000, Gent, Belgium under accession number LMBP 5447CB.

*C. elegans* nuc-1(e1393): *C. elegans* strain with a reduced endonuclease activity (>95%); condensed chromatin persists after programmed cell death; ingested (bacterial) DNA in the intestinal lumen is not degraded. Several alleles are described: e1392 (strong allele: has been used for the experiments described below); n887 (resembles e1392) and n334 (weaker allele). References: Stanfield et al. (1998) East Coast Worm meeting abstract 171; Anonymous, Worm Breeder's Gazette 1(1):17b; Hevelone et al. (1988) Biochem. Genet. 26:447–461; Ellis et al., Worm breeder's Gazette 7(2):44; Babu, Worm Breeder's gazette 1(2):10; Driscoll, (1996) Brain Pathol. 6:411–425; Ellis et al., (1991) Genetics 129:79–94.

The *C. elegans* gun mutant strain bg85 was deposited on Dec. 23, 1999 in accordance with the provisions of the Budapest Treaty on the International Recognition of the Deposit of Microorganisms in the Belgian Coordinated Collections of Microorganisms-BCCM LMBP- Collection, Universiteit Gent, K. L. Ledeganckstraat 35, B-9000, Gent, Belgium under accession number LMBP 5334CB.

Characteristics of *E. coli* strain HT115 (DE3):—F—mcrA mcrb IN(rrnD-rrnE) 1 λ—rnc14::tr10 (DE3 lysogen: lacUV5 promoter-T7polymerase); host for IPTG inducible T7 polymerase expression; RNaseIII; Fire A, Carnegie Institution, Baltimore, Md., Pers. Comm.

*C. elegans* strains, wild type (N2), or selected mutants or transgenics are grown on agar plates as known in the art (Methods in Cell Biology, vol. 48, 1995, "*Caenorhabditis elegans*: Modern biological analysis of an organism" Eds. H. F. Epstein and D. C. Shakes, Academic Press).

Various methods can be used to dispense nematode worms into the wells of a multi-well microtiter plate ensuring that substantially equal numbers of worms are added to each of the wells. One way in which this can be achieved is by taking worms cultured according to the standard procedures known to those skilled in the art in solid or liquid media and re-suspending the worms in a viscous solution to form a homogeneous suspension. The viscosity of the solution maintains an even distribution of worms in the suspension, thus substantially equal numbers of worms can be dispensed by adding equal volumes of the homogeneous worm suspension to each of the wells. Suitable viscous solutions include a solution containing a low concentration of a polymer material (e.g. 0.25% low melting point agarose), glycerol etc.

Alternatively, an equal distribution of worms over the wells of the multi-well plate can be achieved using a 'worm dispenser apparatus' which is commercially available from Union Biometrica, Inc, Somerville, Mass., USA. The worm dispenser can be programmed to add a set number of worms to each of the wells of the plate. In addition, it can be used to select worms in such a way that only hermaphrodites or males or dauers are dispensed and it can also select on the basis of size so that specifically eggs, L1, L2, L3, L4 or adult worms are dispensed.

Probes to detect the lipid uptake consist mainly of a lipid labelled with a detectable marker. Such a marker may be a luminescent, or a colored marker, but is preferentially a fluorescent marker. Labelled lipids can be purchased commercially from Molecular Probes, Eugene, Oreg., USA. Lipids which are labelled with BODIPY, DPH, NBD, Pyrene or Perylene are of particular interest, but other fluorescent labels such as Fluorescein, or Texas red could be used in the assays of the invention. A process for the synthesis of quenched probes is given below.

Example 1

Fatty Acid Uptake Assay Using Agar Plates

1) Basic Methodology

The probe incubation step may be performed on agar plates as follows:

Prepare standard agar plates for growth of nematodes (e.g. *C. elegans*) seeded with a food bacterium such as *E. coli*. Add 50 $\mu$M of probe, diluted in 1 ml of M9 medium directly onto the *E. coli* layer on the agar plate. Add synchronised nematodes onto the plate and incubated in the presence of the probe for the appropriate length of time. The plates should be incubated in the dark at an appropriate temperature, which might vary depending on the precise application of the method. The length of the incubation is usually approximately one hour, the optimum incubation being determined empirically for any given experiment.

The worms are then collected from the plates and centrifuged at 1000 rpm for 5 minutes in a 15-ml conical tube. The pellet is rinsed by re-suspension in approximately 10 ml of M9. The operation is repeated 3 times to ensure elimination of the non-incorporated probe.

Probe uptake is then determined as follows:

Approximately 50 nematodes per well are distributed into a black microtiter plate in triplicate. Fluorescence intensity can then be measured in a microtiter plate reader using standard fluorescein filters. The black microtiter plates are essentially the same as conventional microtiter plates but manufactured in black plastic. Black plates are used so that no fluorescence interference is measured from the neighbouring wells next to the well which is measured. Many manufacturers supply such plates, for example Polylabo, Strasbourg, France.

2) Choice of Probe (FIG. 1)

Standard agar plates for growth of nematodes were prepared. On the *E. coli* layer, 1 ml of 50 $\mu$M BODIPY® probes solute in DMSO was added (Molecular Probes, Eugene, Oreg.), and synchronized worms were placed on the agar plates. The plates with the worms were incubated for 60 to 120 minutes in the dark at the appropriate temperature. BODIPY 500/510 was used as a blank control.

After incubation, the worms were collected in 15 ml of M9 medium (6 g $Na_2HPO_4$, 3 g $KH_2PO_4$, 5 g of NaCl, 1 ml of $MgSO_4$ 1M, add $H_2O$ up to 1 l) and the worms pelleted by gentle centrifugation. The supernatant was aspirated and the worms are washed 3 times with 15 ml of M9. The worms were then dispensed with the COPAS Worm Dispenser, 50 worms per well, in a 96 well black U-shaped microtiter plate, in triplicate for each different population/condition.

After dispensing the worms into the wells the fluorescence intensity was measured using a standard microtiter plate reader. The fluorescence intensity observed can be correlated directly to the probe uptake, and hence to the fatty acid-uptake. From the results shown in FIG. 1 it is clear that, at least in this kind of assay, $C_4$-BODIPY 500/510 $C_9$ is the probe of choice.

Figure 2:
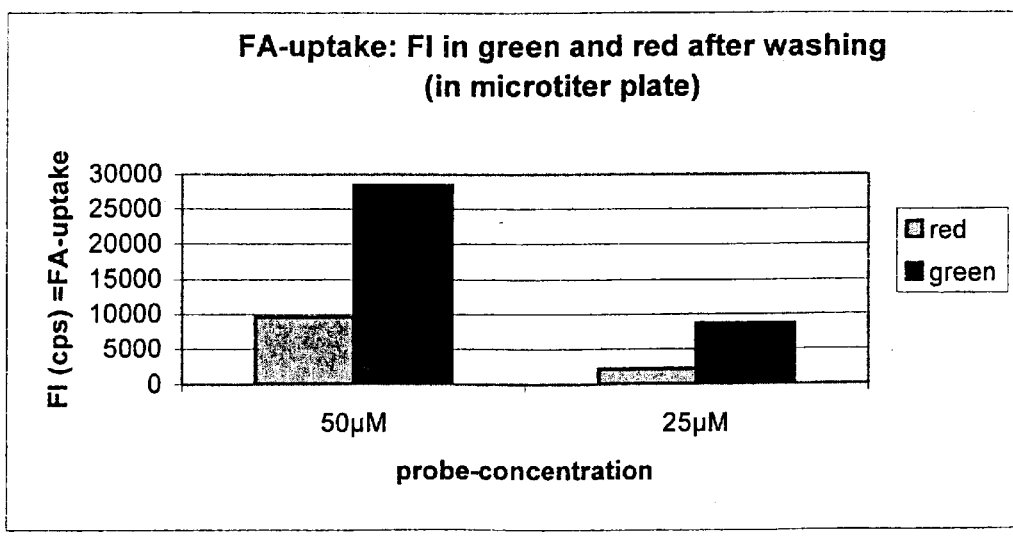
FIG. 2 is a graph to illustrated the effect of probe concentration in a fatty acid uptake assay.

3) Probe Concentration (FIG. 2)

90 $\mu$l worms were incubated with 10 $\mu$l of probe of different concentrations in the wells of a black microtiter plate. After 1 h of incubation, the plate was washed (8×) to remove the background and fluorescence measured in the green (fluorescein filters; 485/535 nm) and in the red (485/590 nm). The results of this experiment, shown in FIG. 2, indicate that a probe concentration of 50 $\mu$M can be considered as optimal.

Figure 3:
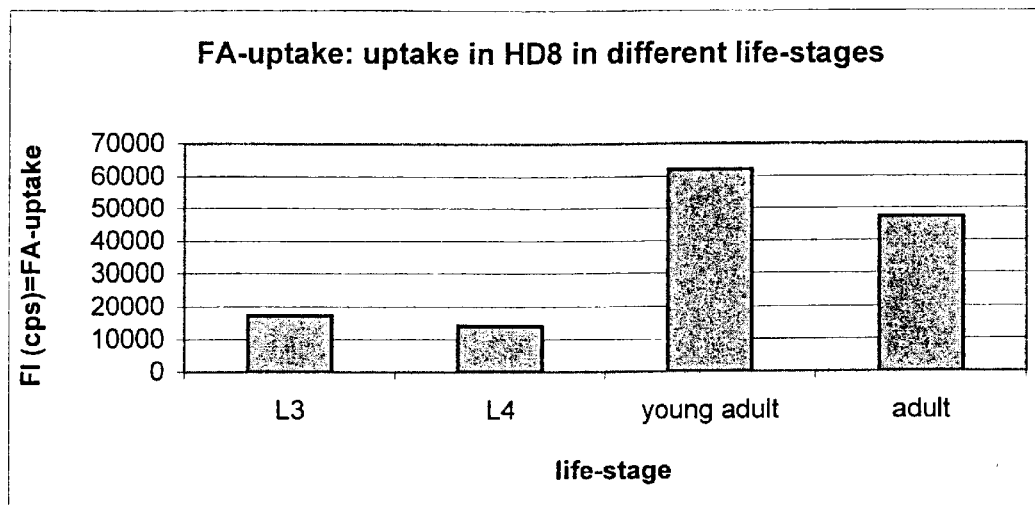
FIG. 3 is a graph to illustrate the variation in fatty acid uptake in different stages of the life cycle of C. elegans strain HD8.
Figure 4:
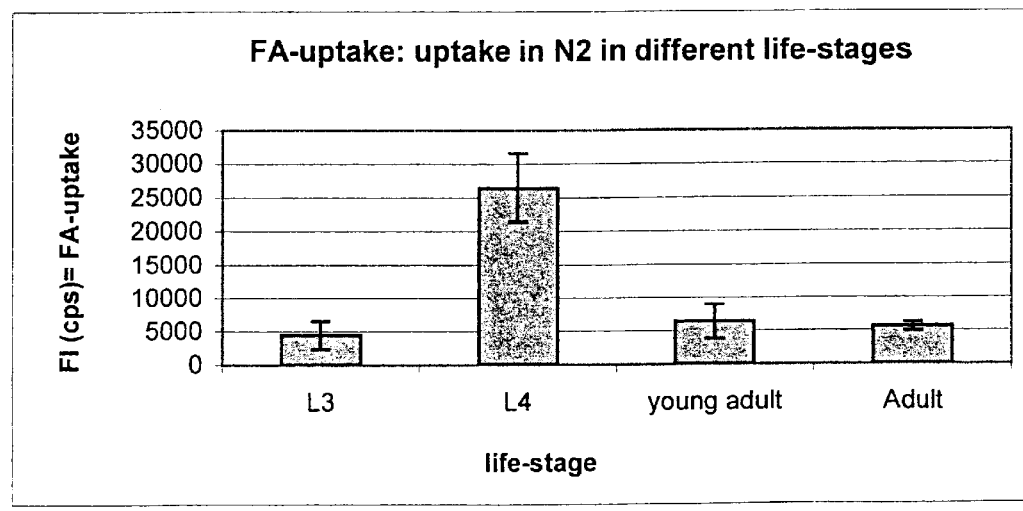
FIG. 4 is a graph to illustrate the variation in fatty acid uptake in different stages of the life cycle of C. elegans wild-type strain N2.

4) Life-Stage (FIG. 3, FIG. 4)

N2 wild type worms and HD8 constitutive pharynx pumping worms were collected at different life-stages. The worms were further incubated for 1 h with 30 $\mu$M probe in 1 ml M9 on agar plates. After incubation the worms were washed, and dispensed with the wormdispenser 50 worms per well in a black microtiter plate and fluorescence intensity measured using a microtiter plate reader. The results of this experiment shown in FIGS. 3 and 4 clearly indicate that fatty acid uptake is dependent on the *C. elegans* strain. The optimal uptake hence needs to be defined for every *C. elegans* strain.

Figure 5A:
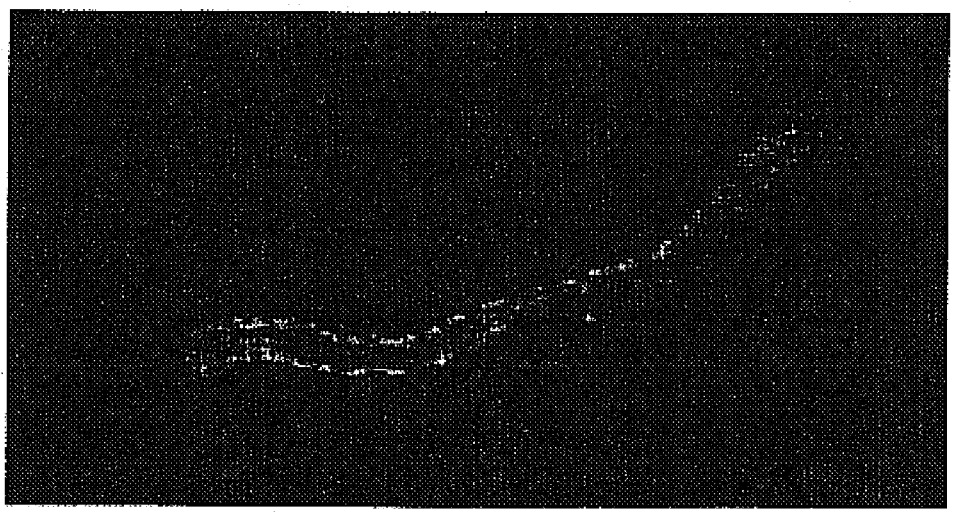
FIG. 5 shows two dissecting microscope images of C. elegans worms incubated in the presence of a labelled lipid probe. After a relatively short incubation it is clearly seen that probe fluorescence is unevenly distributed (FIG. 5(a)); after a longer incubation (FIG. 5(b)) accumulation and distribution of the probe to other parts of the C. elegans body is observed.
Figure 5B:
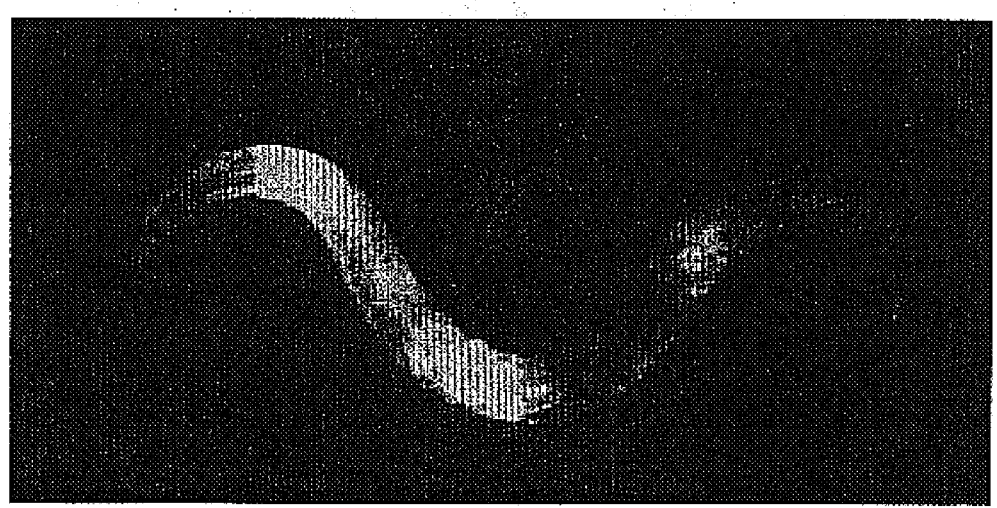

Visual observations of the gut staining in *C. elegans* can be done by GFP dissecting microscope. Probe uptake shows in the green staining of cells in the gut. During the process of probe uptake, it is clearly seen that the uptake of the probe is unevenly distributed. Some cells are more equipped for the uptake of the probe than other cells, indicating that cells in the *C. elegans* gut have specific functional tasks. This allows the development of special screens and assays. After a longer incubation accumulation and distribution of the probe to other parts of the *C. elegans* body is observed (FIG. 5).

Example 2

Assay for Fatty Acid Uptake in Multiwell Plates

This assay is quite analogous to the assay described in Example 1 above, but all stages of the assay are performed in multi-well plates.

Nematode worms may be dispensed into the wells microtiter plates either from a homogeneous suspension of worms (i.e. adding equal volumes of the suspension to the wells of the plates to ensure substantially equal numbers of worms are added to each well) or directly using a worm sorter such as the Wormdispenser from UBI, USA. The first technique allows a faster distribution whereas the second is more accurate as the number of worms can be controlled (i.e. counted). In any case, the amount of worms added to each well is reasonably homogeneous throughout the microtiter plate, thus allowing the reference to control wells (non-treated).

A fixed amount of probe is then distributed in the microtiter wells. The nematodes are incubated for one hour at room temperature in presence or absence of molecules to be tested. The microtiter plate is rinsed 3 to 4 times, using a standard plate washer (Wellwash, Labsystems, Zellik, Belgium), taking care to perform the aspiration sufficiently distant from the bottom of the well to avoid any loss of nematodes remaining at the bottom. The fluorescence intensity is then measured using a fluorescence microtiter plate reader, using a standard set of fluorescein filters.

Example 3

Screening for Compounds that Alter Fatty Acid Uptake

Chemical compounds can be tested using either the plate assay or the multi-well assay in order to identify compounds which alter the uptake of the labelled probe and hence alter fatty acid uptake. In both assays (plate and microtiter plate assay, test compounds are added to the nematodes prior to the addition of the probe.

The length of the incubation of the nematodes with the test compound may be varied in order to select for compounds which act on different types of molecular targets. In order to selectively identify compounds which alters the activity of the fatty acid uptake transporter molecules or that alters the activity of the direct regulators thereof, the nematodes will generally be incubated with the compound for one to two hours prior to the addition of the probes. In order to selectively identify compounds which alter the expression of the transporter proteins or that alters the expression of regulatory transcription factors, or receptor proteins, the nematodes will generally be incubated with the compound for three to sixteen hours prior to the addition of the probes.

Example 4

Figure 6:
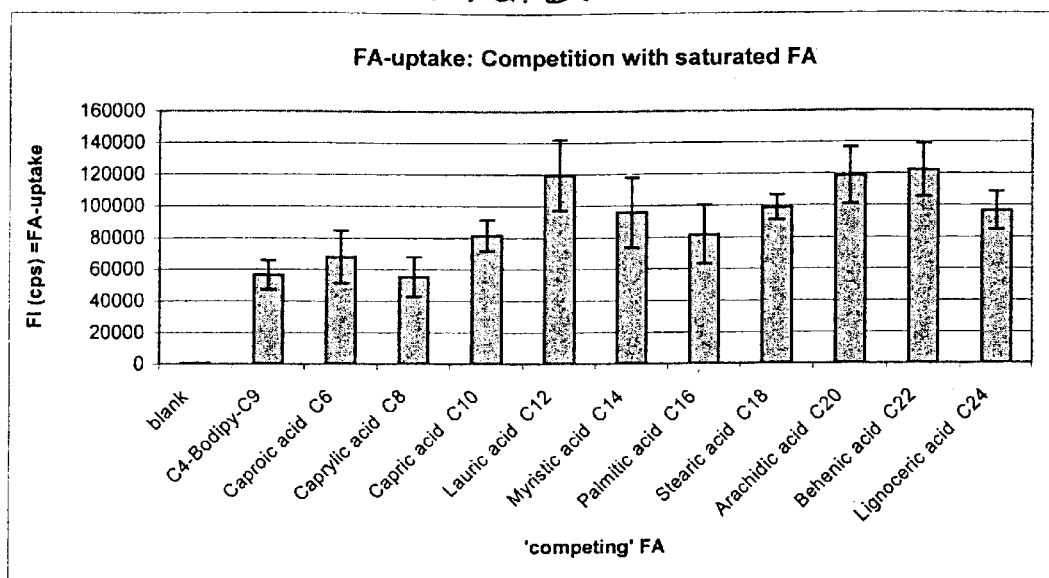
FIG. 6 shows the result of a competition experiment with probe $C_4$-BODIPY-$C_9$ and various competing saturated fatty acids.
Figure 7:
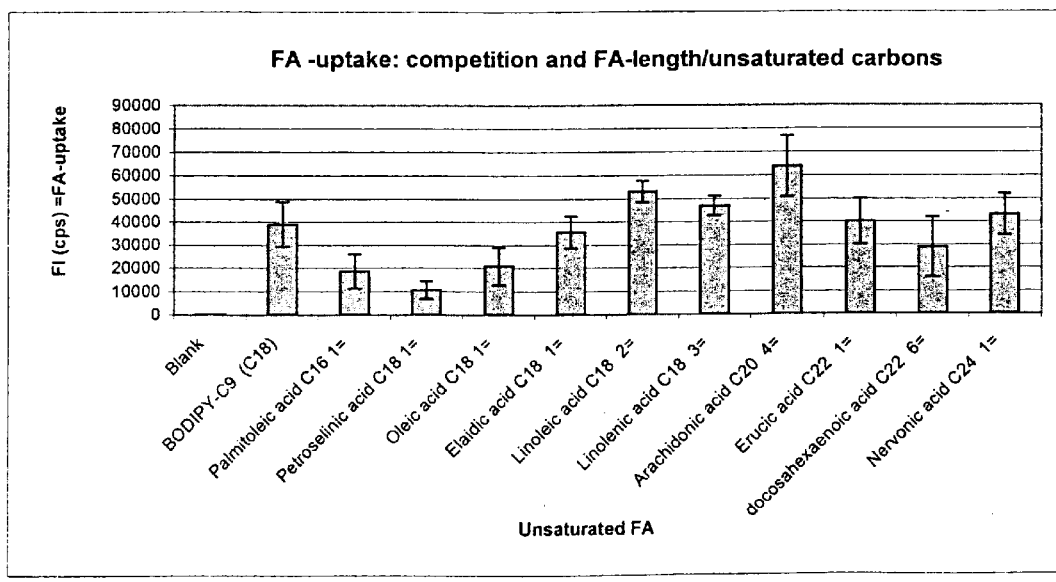
FIG. 7 shows the result of a competition experiment with probe BODIPY-$C_9$ (C18) and various competing unsaturated fatty acids.

Competition Assays (FIG. 6, FIG. 7)

Saturated and unsaturated fatty acids of various chain lengths were incubated in a 5-fold excess compared to the fluorescent probe. The nematodes were processed as described in the microtiter plate assay. This method allows determination of the selectivity of the probe and the selectivity of the fatty acid uptake. If the fatty acid added to the experiments prevents, inhibits or diminishes the uptake of the labelled probe, then one may conclude that the probe is specific for at least this fatty acid. This competition method allows the selection of specific probes, or of general probes. In the competition assays with C4-BODIPY 500/510 $C_9$, no competition was observed with saturated fatty acids, while unsaturated fatty acids clearly show competition (FIG. 7). More particularly, the unsaturated fatty acids with one double bond show the highest competition.

Example 5

Figure 8:
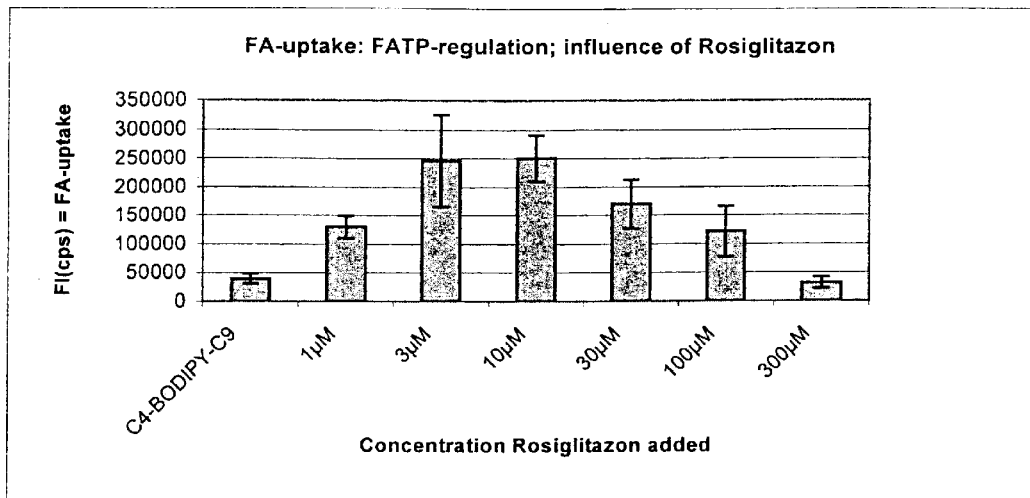
FIG. 8 is a graph to show the influence of Rosiglitazon on fatty acid uptake in C. elegans.
Figure 9:
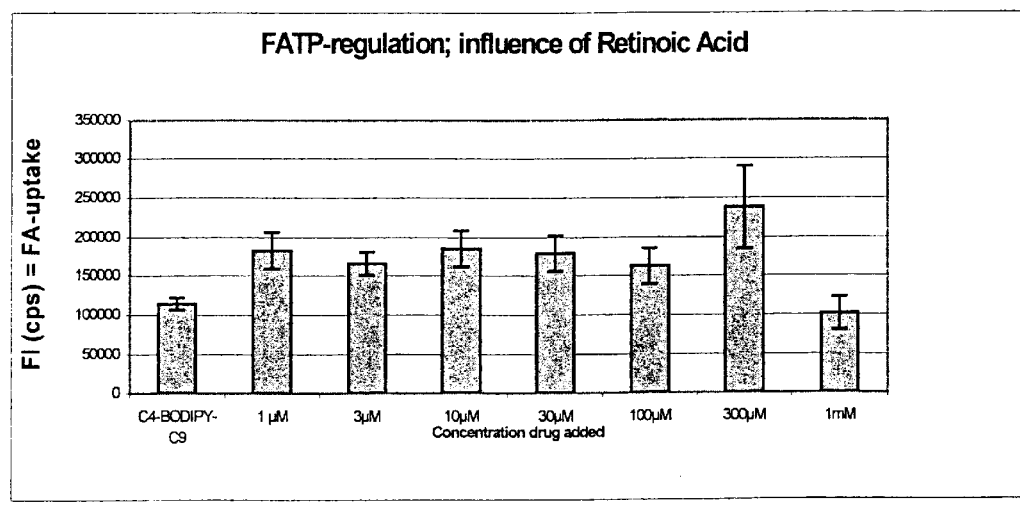
FIG. 9 is a graph to show the influence of Retinoic acid on fatty acid uptake in C. elegans.

Activation of FATPs (FIG. 8, FIG. 9)

Retinoic acid and troglutazones are activators of RXR and PPARγ respectively. C. elegans worms were incubated with these compounds in a range from 100 µM to 0.1 µM for a time period between 1 to 6 hours. Fatty acid uptake was measured using the microtiter plate assay described above.

More particularly, constitutive pharynx pumping worms in late L4 stage or young adults were incubated overnight on agar plates with different concentrations of the retinoic acid or troglutazone (e.g. Rosiglitazon). The compounds were added as solutions in 1 ml M9. After overnight incubation, these worms were further incubated for 1 h with 50 µM $C_4$-BODIPY-$C_9$ in 1 ml M9 on the same agar plates. After incubation the worms were washed three times and dispensed with the worm dispenser, up to 50 worms per well in the multi-well plates. Fluorescence intensity was measured using a microtiter plate reader, as described above. The results of this experiment are shown in FIGS. 8 and 9.

A clear up-regulation of FATP is observed by applying Rosiglitazon, observed as a 5-fold increase in fatty acid uptake. Remarkably this increase was also observed by only applying 3 µM of Rosiglitazon. The up-regulation observed with Retinoic acid is less clearly concentration dependent in the concentration range applied. However, an increase of 60% to 100% fatty acid uptake is observed, showing clearly the up-regulation of FATP.

Example 6

Figure 11:
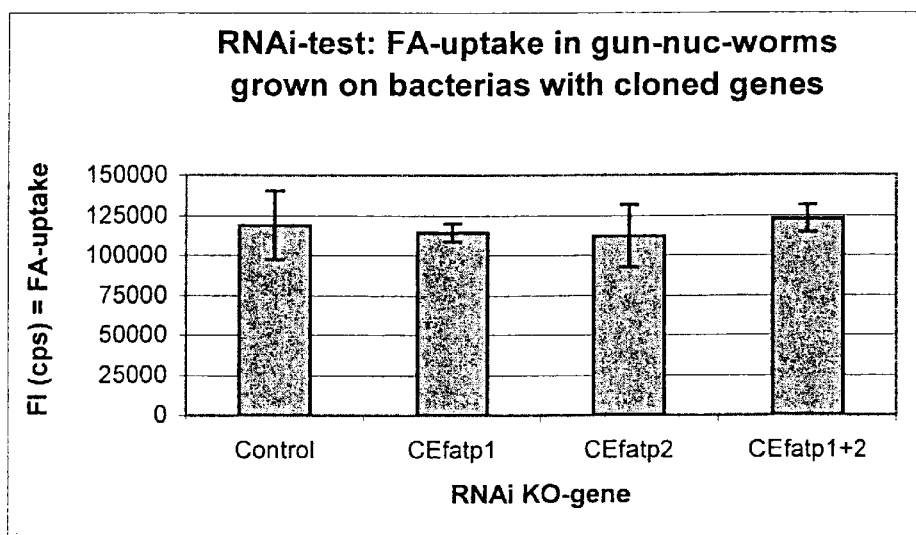
FIG. 11 illustrates the effect of inhibition of expression of the CEfatp1 gene, the CEfatp2 gene or both genes on fatty acid uptake in C. elegans. In each case, gene expression was inhibited using RNAi.

Inactivation of FATPs by RNAs (FIG. 10, FIG. 11)

A vector was constructed that allows for the production of high quantities of dsRNA, corresponding to the C. elegans genes CEfatp1 and CEfatp2. The latter is considered to be the C. elegans homologue of FATP4. A C. elegans nuc-gun strain was then fed with bacteria expressing this dsRNA resulting in RNA inhibition for this gene. Uptake of labelled probe was then followed in this strain. NB. The nuc-gun strain is a double mutant particularly suited to RNAi experiments because it carries both a nuc-1 mutation (reduced expression of nuclease) and a gun mutation (increased gut uptake of nucleic acid). A protocol for the selection of nuc-gun strains is included herein. However, the use of a nuc-gun strain is not essential.

A set of primers was developed to clone coding regions of CEfatp1 and CEfatp2:

```
CEfatp1:
oGN87 (SEQ ID NO:3)
5'-gtgaaggttacaaaatgggcgacgttgtcg-3' oGN88 (SEQ ID NO:4)
5'-cgtcacagcgacacagtacattggagaaatc-3'

CEfatp2:
oGN89 (SEQ ID NO:5)
5'-gaattcttggagttgggcaagctctgttgg-3' oGN90 (SEQ ID NO:6)
5'-cgaggcaattcttcatccaattactggattg-3'
```

Standard PCR amplification using the primer sets given above and Wild-type C. elegans (N2) DNA as template resulted in the amplification of 731 bp PCR product containing exons 5 and 6 for CEfatp1, and amplification of a 962 bp PCR product containing part of exon 6, exon 7 and a part of exon 8 for CEfatp2.

These PCR fragments were linked to BstXI adaptors supplied Invitogen, Groningen, The Netherlands, following the protocol provided by the manufacturer. The resulting fragments were then cloned into the vector pGN29 digested with BstXI, resulting in the plasmids pGX5 and pGX6 respectively. pGN29 is a cloning vector developed by the inventors for use in the production of high quality dsRNA for RNAi experiments. A key feature of the vector is the presence of two opposable T7 promoters which drive the transcription of complementary RNA strands. Any other vector suitable for the production of dsRNA (e.g. plasmid pGN9 described in the co-pending application WO 00/01846) could have been used.

Worms were grown for 2 generations on agar plates and fed on E. coli HT115 bacteria harboring the plasmids pGX5, pGX6 or on a mixture containing both bacteria. DsRNA was induced in these bacterial strains by adding IPTG to the agar plates. After this period, the worms (adult) were incubated for 2 h with 50 µM $C_4$-BODIPY-$C_9$ on the same agar plates. After incubation the worms were washed three times, and dispensed into the wells of a black microtiter plate. Fluorescence intensity was then measured using a microtiter plate reader as described above.

Although the increased expression of FATP by applying troglutazone resulted in a clearly enhanced fatty acid uptake, this reduction of expression experiment did not result in a significant decrease in fatty acid uptake, probably due inefficiency of the RNA inhibition.

Example 7

Figure 12:
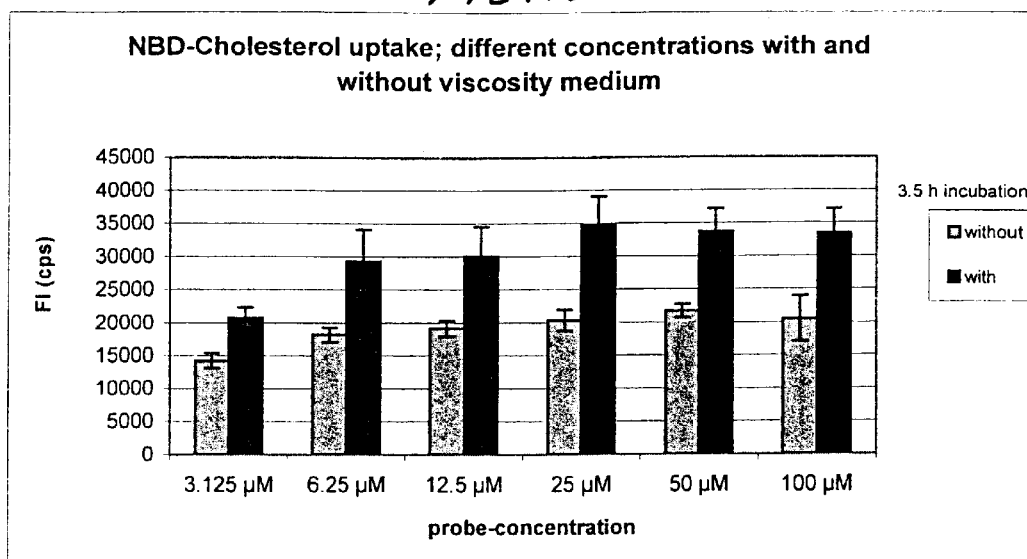
FIG. 12 illustrates the effect of probe concentration and viscosity of the medium on uptake of labelled cholesterol (NBD-cholesterol) in C. elegans.
Figure 13:
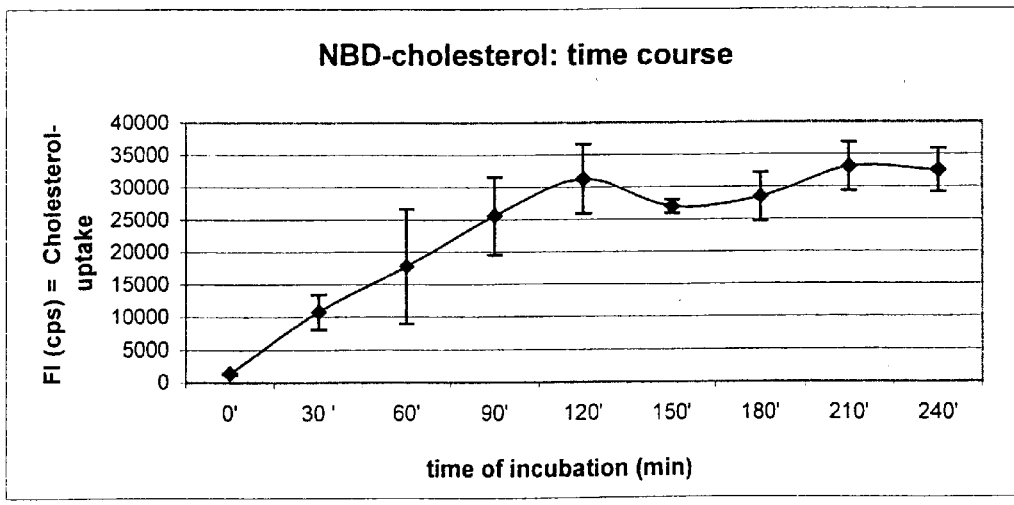
FIG. 13 shows a time course for uptake of NBD-cholesterol in C. elegans, y-axis fluorescence intensity (FI, cps), x-axis probe concentration.
Figure 16:
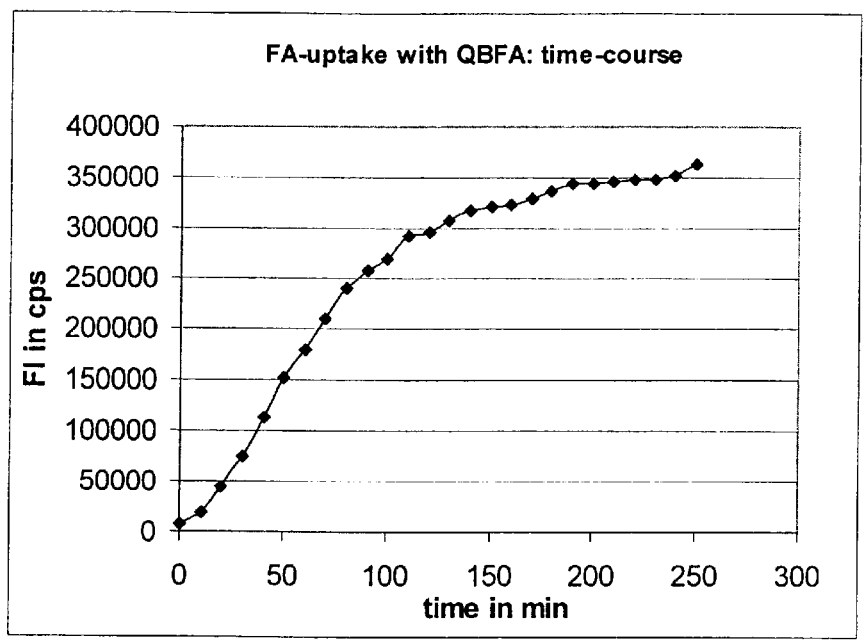
FIG. 16 illustrates a time course for uptake of quenched probe in liquid culture using C. elegans strain HD8. x-axis is fluorescence in cps, y-axis is time in minutes.

Cholesterol Uptake (FIG. 12, FIG. 13)

1) Choice of Probe

As probe to measure cholesterol uptake by C. elegans, NBD-cholesterol (N1148, Molecular probes) was used.

2) Probe Concentration

Approximately 50 worms were added per well to a black microtiter plate and incubated in the presence of 10 µl of probe at different concentrations for 3.5 hours.

Cholesterol uptake was then measured using M9 medium, and M9 with a medium viscosity carboxymethyl cellulose (CMC) at a final concentration of 0.4% (Sigma). After incubation, the worms were paralyzed by adding ivermectin up to a final concentration 3 µM. The plate were washed twice prior to fluorescence measurements.

The results of this experiment (FIG. 12) clearly show that 25 µM of NBD-cholesterol is optimal as final probe concentration. Furthermore, the addition of CMC improves the uptake of cholesterol.

3) Incubation Time

To determine the optimal incubation time, constitutive pharynx pumping worms (strain HD8) were incubated with 10 µl of 250 µM probe (25 µl final), and measured at different time intervals. The results of this experiment (FIG. 13) clearly show that 2 h is the optimal incubation time to measure cholesterol uptake in C. elegans.

Example 8

Application of Quenched Labelled Phospholipids

The use of fluorescent labelled lipids, and also lipids labelled with other markers has the disadvantage that they will provide for high background fluorescence. Although the undigested lipids are washed away in the assay, due to their lipid nature, they tend to stick to the wall of the microtiter plates, resulting in an undesirable background. Fluorescent labels such as BODIPY tend to have a higher fluorescence when contacted with itself. Furthermore, an emission shift can be observed from green fluorescence to red fluorescence, at high concentrations. Fluorescent labels such as NBD, tend to have a very low fluorescence in solution, when intercalating into membranes or in other lipid environments, NDB has a higher fluorescence. For this reason, these markers are preferred by the inventors. Because of the low background fluorescence of these markers, it is easier to distinguish selectively between probe that has been taken up by the worms and probe that is still free in the medium, leading to an overall improvement in the performance of the assay.

Use of probes with a lower background fluorescence means that the number of washing steps in the assay procedure can be reduced. The presence of probe sticking to the walls of the microtiter plates is also less disturbing to the assay.

Dinitrophenyl is known to quench the fluorescent BODIPY group. As has been shown by Hendrickson et al. (Anal. Biochemistry, 1999, 276:27–35) lipid analogues harboring a BODIPY group and a dinitrophenyl group can easily be synthesized. Thuren et al. (Anal Biochemistry, 1998, 170:248–255) synthesized phospholipid analogues with a fluorescent pyrenehexanoyl group and a quenching trinitrophenyl group. This quenched fluorescent lipid analogue can also be easily synthesized. These double labelled lipids may be used to construct a improved assay. Ideally, dinitrophenyl group should linked to the lipid by a bond that is readily hydrolyzed, for instance by intestinal enzymes such as esterases or proteases. Such a probe will have no or only very low background fluorescence in the assay medium. Upon hydrolysis of the bond linking the quenching (e.g. dinitophenyl) group to the lipid, the probe becomes fluorescent, resulting in a clear signal.

The protocol to perform lipid uptake assays with quenched probes is analogous to previously described assays, with the advantage that the number of washing steps may be reduced because the background fluorescence of the probe is lower.

Example 9

Synthesis of a Quenched Probe N-(2,4-dinitrophenyl), O-(5-butyl-4,4-difluoro-4-bora-3a, 4a-diaza-s-indacene-3-nonoyl)-ethanolamine a) Synthesis of N-(2,4-dinitrophenyl)ethanolamine A mixture of 3.0 g of 2,4-dinitrofluorobenzene (16.12 mmol, 1 eq) and 1.17 ml ethanolamine (19.34 mmol, 1.2 eq) in acetonitrile (30 ml) with 3.56 g of $K_2CO_3$ (25.79 mmol, 1.6 eq) was heated at 65° C. overnight. The reaction mixture became red. The solvent was removed under reduced pressure. The residue was diluted in 1N $Na_2CO_3$ and extracted with ethyl acetate (5×50 ml). The combined organic layer was washed with saturated NaCl (3×20 ml), dried over $MgSO_4$ and concentrated under reduced pressure. To this orange solution was added ethanol (20 ml) and the mixture was heated at 80° C. until dissolution was complete. Distilled water (20 ml) was added and the solution was cooled to room temperature over a period of 1 hour. The yellow solid which crystallized was collected by filtration, washed with 30/70:ethanol/water and then distilled water (2×30 ml). The solid was dried by lyophilization.

b) Synthesis of N-(2,4-dinitrophenyl), O-(5-butyl-4,4-difluoro-4-bora-3a,4a-diaza-s-indacene-3-nonoyl)-ethanolamine 5-butyl-4,4-difluoro-4-bora-3a,4a-diaza-s-indacene-3-nonanoic acid ($C_4$-BODIPY® 500/510 $C_9$, obtained from Molecular Probes, Inc., 10.00 mg, 0.0247 mmol, 1 eq) was placed in a Kimble tube. N-(2,4-dinitrophenyl) ethanolamine (6.24 mg, 0.0275 mmol, 1.11 eq) was added followed by dichloromethane (0.247 ml) containing 4-N,N-dimethylaminopyridine (0.608 mg) then followed by ethyl-3-dimethylaminopropylcarbodiimide hydrochloride (7.10 mg). The solution was stirred at room temperature overnight. The reaction was analyzed by LCMS which confirmed that the acid was completely consumed. Only the excess of N-(2,4-dinitrophenyl)ethanolamine was detected. The reaction mixture was purified by flash chromatography on silica gel (3 g) using a 10 ml syringe with fritte and dichloromethane as eluant to provide the title compound in a yield of 99.6% at a purity of 97.7%.

Example 11

Experiments Using a Quenched Probe

Experiments (i) to (iii) were designed to investigate the effect of varying the incubation time, probe concentration and numbers of C. elegans per well in a basic lipid uptake assay using a quenched probe in liquid culture.

Experiment (i)-Effect of Incubation Time

Figure 17:
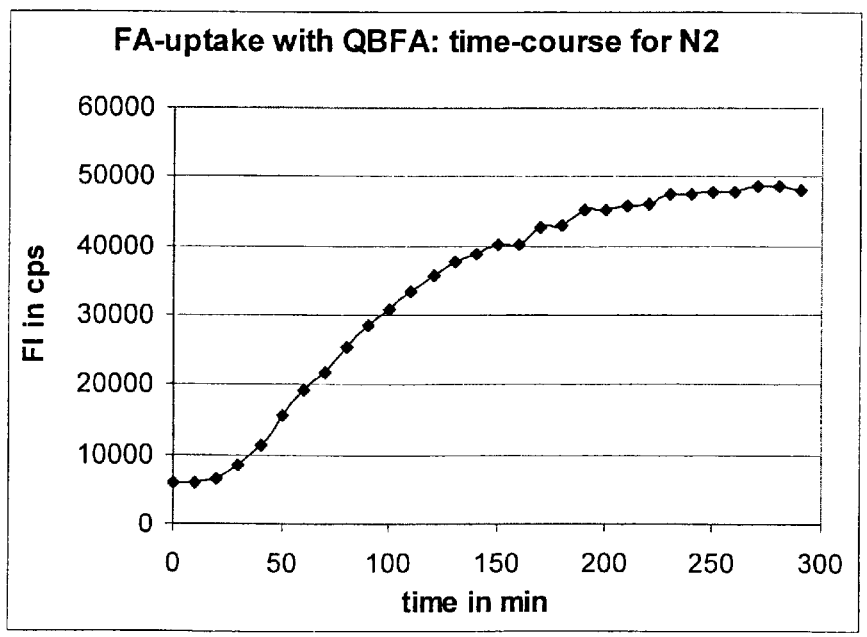
FIG. 17 illustrates a time course for uptake of quenched probe in liquid culture using wild type (N2 strain) C. elegans. x-axis is fluorescence in cps, y-axis is time in minutes.
Figure 18:
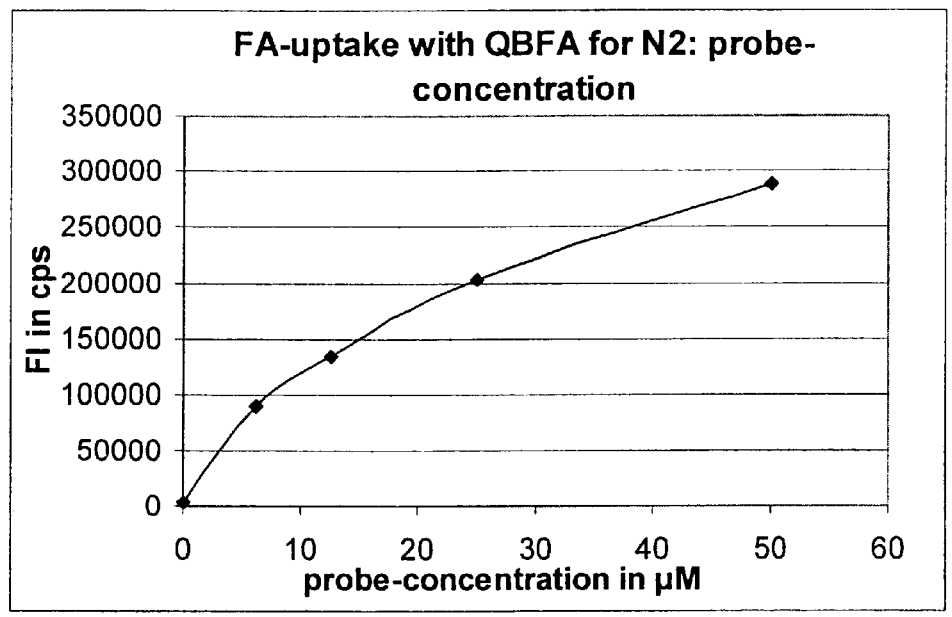
FIG. 18 illustrates the effect of probe concentration for uptake of quenched probe in liquid culture using wild type (N2 strain) C. elegans. x-axis is fluorescence in cps, y-axis is probe concentration in $\mu$M.

Approximately 100 to 150 C. elegans worms were placed per well into a microtiter plate. When using C. elegans strain HD8 adult worms were used, whereas when using wild-type C. elegans L4 stage worms were used. 25 µM of quenched probe was added in a final volume of 100 µl M9 medium. The microtiter plates were then placed in an automatic fluorescence reader and the fluorescence measured at various time intervals after addition of the probe. Typical results are shown in FIG. 17 and FIG. 18.

The results of this experiment show that probe uptake and detection of fluorescence can be measured over a broad range of time. Both for the wild-type strain and for the HD8 strain, fluorescence may be detected from less than 30 minutes up to more than 300 minutes after addition of the probe.

Experiment (ii)-Effect of Probe Concentration

Figure 19:
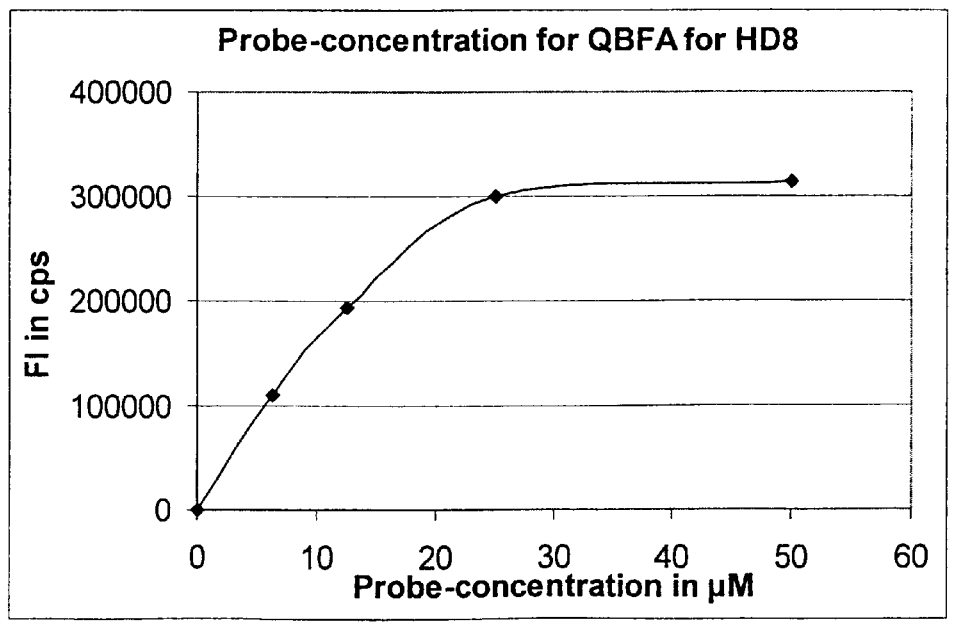
FIG. 19 illustrates the effect of probe concentration for uptake of quenched probe in liquid culture using C. elegans strain HD8. x-axis is fluorescence in cps, y-axis is probe concentration in $\mu$M.

Approximately 100–150 young adult *C. elegans* were placed per well in a micro-titer plate. Several concentrations of the quenched probe were added (10–60 μM final concentration) in a total volume of 100 μl M9 medium. The micro-titer plates were incubated for three hours at room temperature, prior to measurement of the fluorescence in an automated reader. Typical results are illustrated in FIG. 18 and FIG. 19.

The results of this experiment show that probe uptake and fluorescence detection can be performed at varying concentrations of the added probe (QBFA). Similar results are obtained with wild-type *C. elegans* and with the HD8 strain. The results show that the optimal probe concentration for the wild-type strain ranges from less than 5 μM up to more than 50 μM in this assay system, optimal probe being defined as the lowest concentration of probe giving the highest read-out. The HD8 strain is more sensitive in detection of the probe, hence the optimal probe concentration ranges from less than 5 μM up to more than 25 μM.

Experiment (iii)-Effect of Varying Number of *C. elegans*

Figure 20:
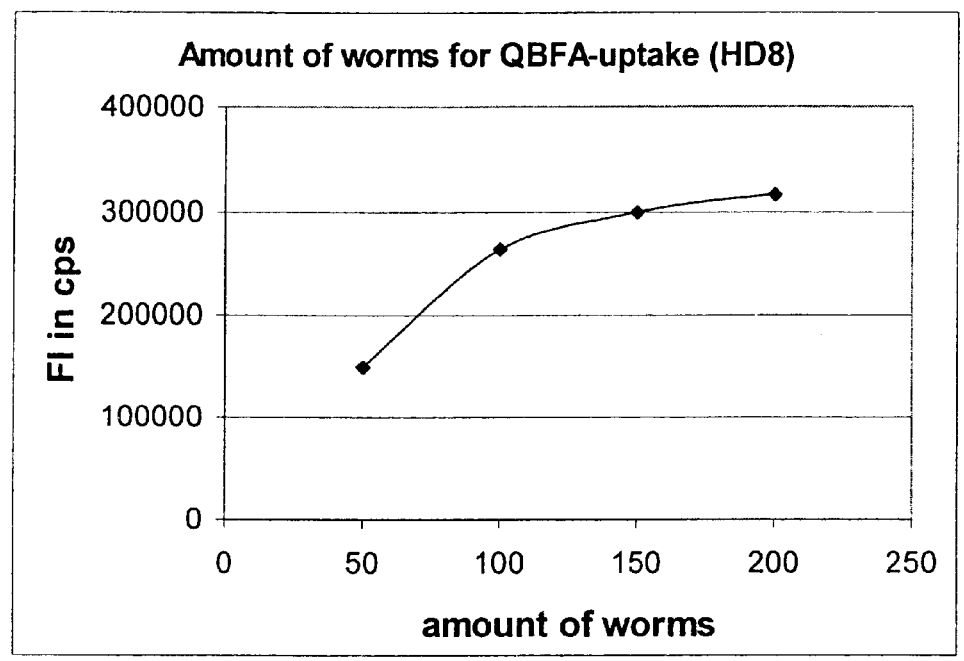
FIG. 20 illustrates the effect of varying the amount of worms added per well for uptake of quenched probe in liquid culture using C. elegans strain HD8. x-axis is fluorescence in cps, y-axis is number of worms added per well.

Varying numbers of HD8 strain *C. elegans* worms were dispensed into the wells of a micro-titer plate. The probe QBFA was added at a final concentration of 25 μM in a total volume of 100 μM M9 medium. The plates were incubated at 20° C. and fluorescence measured in an automated fluorescence reader. Typical results are illustrated in FIG. 20.

The results of this experiment show that using the uptake of the probe can be detected using varying numbers of *C. elegans* worms. In particular, probe uptake can be effectively measured using less than 50 up to more than 200 individual worms per well.

Figure 21:
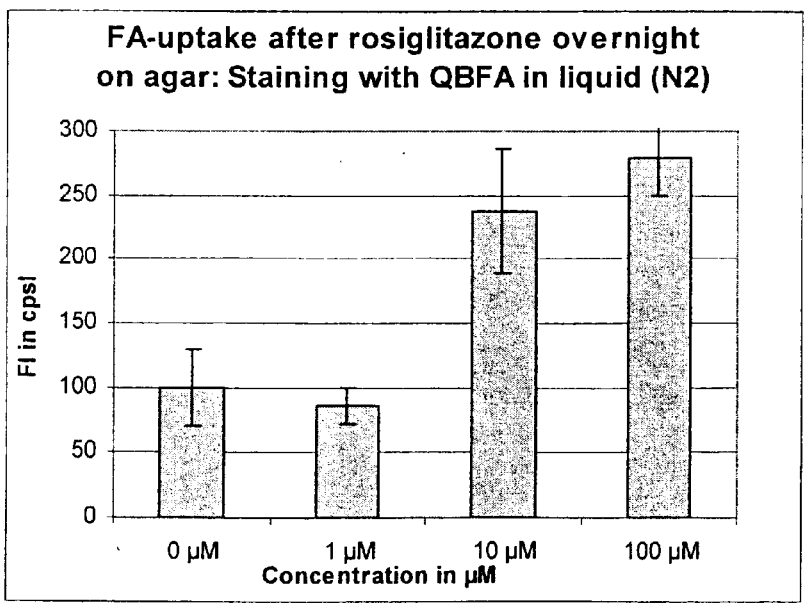
FIG. 21 illustrates the effect of rosiglitazone in a lipid uptake assay using wild type (N2) C. elegans. Overnight incubation of the worms with varying concentrations of rosglitazone was carried out on agar plates. Staining with the quenched probe was carried out in liquid culture.

Experiment (iv)-To Show Utility of the Lipid Uptake Assay for Identification of Compounds Having an Effect on Lipid Uptake Standard 9 cm agar plates were seeded with *E. coli* (any strain suitable for use in culture of *C. elegans* may be used). 1 ml volume of rosiglitazone at various concentrations was added to the plates and the plates seeded with L4 stage *C. elegans*. After an overnight incubation (approximately 16 h), the *C. elegans* were isolated and washed three times with approximately 15 ml M9 buffer. The worms were then re-suspended into microtiter plates, at 100 worms per well. Quenched probe (QBFA) was added at a final concentration of 10 μM in a total volume of 100 μl. Fluorescence measurements were taken after 2 hours in an automated plate reader. Typical results are illustrated in FIG. 21.

The results of this experiment show that the quenched probe can be use to isolate compounds that have an effect on lipid uptake, such as rosiglitazone which is known for its action on PPARγ.

Example 12

Generation of Mutants Resistant to Fatty Acid Uptake

A population of wild-type *C. elegans* nematodes, is chemically mutagenized, for example using EMS, to gen erate a population of mutants covering approximately 20000 genomes. The methodology for this kind of experiments is well known in the art, and has been described in Methods in Cell Biology, Vol 48, *C. elegans*: Modern biological analysis of an organism, Ed. by Epstein and Shakes. The F2 generation is then incubated in the presence of 50 μM of probe. Worms that are not stained by the probe are isolated and cloned on small agar plates. Progenies are examined for staining with various probes to determine the specificity of the mutation. Confirmed mutants, that are specifically resistant to fatty acid uptake can then be used for screening hit confirmation and/or identification of fatty acid transport proteins in *C. elegans* intestine. It is considered a matter of routine in the *C. elegans* field to isolate the gene or genes which are mutated in a specific mutant *C. elegans* strain.

Example 13

Selection of a gun-nuc Double Mutant *C. elegans* Strain

As an example, the crossing strategy of gun(bg85) with nuc-1 is shown.

| | |
|---|---|
| P0 cross: | gun (bg85) × WT males |
| F1 cross: | nuc-1 × gun (bg85)/+ males |
| F2 cross: | nuc-1 × gun (bg85)/+; nuc-1/0 males (50%) |
| | nuc-1 × +/+; nuc-1/0 males (50%) |
| F3 single: | gun (bg85)/+; nuc-1 hermaphrodites (25%) |
| | +/+; nuc-1 hermaphrodites (75%) |
| F4 single: | gun (bg85); nuc-1 (¼ of every 4th plate high staining with BCECF) |
| F5 retest: | gun (bg85); nuc-1 (100% progeny of F4 singled high staining with BCECF) |

To select for the gun phenotype, the fluorescence precursor BCECF-AM is used (obtainable from Molecular probes). The precursor BCECF-AM is cleaved by esterases present in the gut of the worm to generate the dye BCECF which is fluorescent at pH values above 6. This allows selection for worms that have a gun phenotype. BCECF-AM is taken up through the pharynx into the gut lumen and is not fluorescent until it has been cleaved, and the BCECF portion has entered the cells surrounding the lumen. Wild-type worms will show slower or no increase in BCECF fluorescence.

Other aspects of the invention will be clear to the skilled artisan and need not be repeated here. Each reference or publication cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method of assaying lipid uptake into microscopic nematode worms which comprises:
   incubating the microscopic nematode worms in the presence of a probe molecule comprising a lipid moiety linked to a signal generating label; and
   determining the amount of probe molecule taken up by the microscopic nematode worms by detecting a signal generated from the label part of the probe molecule.

2. The method according to claim 1 wherein the microscopic nematode worms are of the genus Caenorhabditis.

3. The method according to claim 2 wherein the microscopic nematode worms are C. elegans or C. briggsae.

4. The method according to claim 1 wherein the step of incubating the microscopic nematode worms in the presence of the probe molecule is carried out on a solid culture medium.

5. The method according to claim 4 wherein the solid culture medium is an agar plate.

6. The method according to claim 1 wherein the step of incubating the microscopic nematode worms in the presence of the probe molecule is carried out in a liquid culture medium.

7. The method according to claim 6 wherein the liquid culture medium is contained in a multi-well plate.

8. The method according to claim 1 which further includes one or more washing steps between the incubation with the probe and determination of the amount of probe molecule taken up by the microscopic nematode worms.

9. The method according to claim 1 wherein the step of determining the amount of probe molecule taken up by the microscopic nematode worms is performed in microtiter plates using a microtiter plate reader.

10. The method according to claim 1 wherein the signal generating label part of the probe molecule comprises a fluorescent, luminescent or coloured label.

11. The method according to claim 10 wherein the signal generating label part comprises 4,4-difluoro-4-bora-3a,4a-diaza-s-indacene (BODIPY), 7-nitrobenz-2-oxa-1,3-diazole (NBD), diphenylhexatriene (DPH), pyrene, perylene, fluorescein or Texas-red.

12. The method according to claim 10 wherein the signal generating label part of the probe molecule comprises a fluorescent label and the probe molecule further comprises a quencher portion which is adapted to quench the fluorescence emitted from the label part.

13. The method according to claim 12 wherein the quencher portion of the probe molecule is cleaved from the remainder of the probe molecule by the action of an enzyme present in the intestinal lumen of the said microscopic nematode worm.

14. The method according to claim 13 wherein the enzyme is a protease or an esterase.

15. The method of assaying lipid uptake into microscopic nematode worms according to claim 12 wherein the probe molecule is a compound of Formula I:

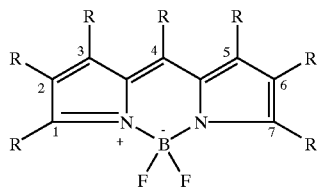

Formula I wherein:
one of the R groups (R') is —A—X—Q, wherein A is a saturated or unsaturated linear $C_{3\text{-}21}$ hydrocarbon chain, X is an enzyme cleavable or enzyme hydrolysable functional group, and Q is a quencher for the 4,4-difluoro-4-bora-3a,4a-diaza-s-indacene portion of the compound;

one of the R groups (R") is selected from the group consisting of H, $C_1$–$C_6$alkyl, $C_2$–$C_6$alkenyl, $C_2$–$C_6$alkynyl, aryl$C_1$–$C_6$alkyl, aryl$C_2$–$C_6$alkenyl, aryl$C_2$–$C_6$alkynyl, aryl, $C_1$–$C_6$alkoxyaryl, heteroaryl and saturated or unsaturated linear $C_3$–$C_{21}$ hydrocarbons; the remaining R groups (R''') are each independently selected from the group consisting of H, $C_1$–$C_6$alkyl, $C_2$–$C_6$alkenyl, $C_2$–$C_6$alkynyl, aryl$C_1$–$C_6$alkyl, aryl$C_2$–$C_6$alkenyl, aryl$C_2$–$C_6$alkynyl, aryl, $C_1$–$C_6$alkoxyaryl and heteroaryl.

16. The method according to claim 1 wherein the lipid moiety of the probe molecule is selected from the group consisting of: a fatty acid, cholesterol, a phospholipid and a triglyceride.

\* \* \* \* \*

SEQUENCE LISTING

<160> NUMBER OF SEQ ID NOS: 6

<210> SEQ ID NO 1
<211> LENGTH: 4162
<212> TYPE: DNA
<213> ORGANISM: Artificial Sequence
<220> FEATURE:
<223> OTHER INFORMATION: Description of Artificial Sequence: Plasmid pGX5

<400> SEQUENCE: 1

| | | | | | |
|---|---|---|---|---|---|
| gtgaaggtta | caaaatgggc | gacgttgtcg | ctttgtttat | ggaaaatagc atcgacttct | 60 |
| ttgcaatttg | gctgggactt | tccaagattg | gagtcgtgtc | ggcgttcatc aactcaaact | 120 |
| tgaagttgga | gccattggca | cattcgatta | atgtttcgaa | gtgcaaatca tgcattacca | 180 |
| atatcaatct | gttgccgagt | aagtttgcag | aaataaatat | accgggatgt ttaaaaatcc | 240 |
| tgcgtggaaa | tggcagatgt | tttacatact | attttttacag | tgttcaaagc cgctcgtgaa | 300 |
| aagaatctga | tcagtgacga | gatccacgtg | tttctggctg | gaactcaggt tgatggacgt | 360 |
| catagaagtc | ttcagcaaga | tctccatctt | ttctctgagg | atgaacctcc agttatagac | 420 |
| ggactcaatt | ttagaagcgt | tctgtgttat | atttacactt | ccggtactac cggaaatcca | 480 |
| aagccagccg | tcattaaaca | cttccgttac | ttctggattg | cgatgggagc aggaaaagca | 540 |
| tttggaatta | ataagtcaga | cgttgtgtac | attacgatgc | caatgtatca ctctgccgcc | 600 |
| ggtatcatgg | gtattggatc | attaattgca | ttcgggtcga | ccgctgttat taggaaaaag | 660 |
| ttttcggcaa | gcaacttctg | gaaagattgc | gtcaagtaca | acgtcacagc gacacagtac | 720 |
| attggagaaa | tcccagcaca | atggatctcg | agggatcttc | catacctacc agttctgcgc | 780 |
| ctgcaggtcg | cggccgcgac | tctctagacg | cgtaagctta | ctagcataac cccttggggc | 840 |
| ctctaaacgg | gtcttgaggg | gttttttgag | cttctcgccc | tatagtgagt cgtattacag | 900 |
| cttgagtatt | ctatagtgtc | acctaaatag | cttggcgtaa | tcatggtcat agctgtttcc | 960 |
| tgtgtgaaat | tgttatccgc | tcacaattcc | acacaacata | cgagccggaa gcataaagtg | 1020 |
| taaagcctgg | ggtgcctaat | gagtgagcta | actcacatta | attgcgttgc gctcactgcc | 1080 |
| cgctttccag | tcgggaaacc | tgtcgtgcca | gctgcattaa | tgaatcggcc aacgcgcggg | 1140 |
| gagaggcggt | ttgcgtattg | ggcgctcttc | cgcttcctcg | ctcactgact cgctgcgctc | 1200 |
| ggtcgttcgg | ctgcggcgag | cggtatcagc | tcactcaaag | gcggtaatac ggttatccac | 1260 |
| agaatcaggg | gataacgcag | gaaagaacat | gtgagcaaaa | ggccagcaaa aggccaggaa | 1320 |
| ccgtaaaaag | gccgcgttgc | tggcgttttt | cgataggctc | cgccccctg acgagcatca | 1380 |
| caaaaatcga | cgctcaagtc | agaggtggcg | aaacccgaca | ggactataaa gataccaggc | 1440 |
| gtttccccct | ggaagctccc | tcgtgcgctc | tcctgttccg | accctgccgc ttaccggata | 1500 |
| cctgtccgcc | tttctccctt | cgggaagcgt | ggcgctttct | catagctcac gctgtaggta | 1560 |
| tctcagttcg | gtgtaggtcg | ttcgctccaa | gctgggctgt | gtgcacgaac cccccgttca | 1620 |
| gcccgaccgc | tgcgccttat | ccggtaacta | tcgtcttgag | tccaacccgg taagacacga | 1680 |
| cttatcgcca | ctggcagcag | ccactggtaa | caggattagc | agagcgaggt atgtaggcgg | 1740 |
| tgctacagag | ttcttgaagt | ggtggcctaa | ctacggctac | actagaagga cagtatttgg | 1800 |
| tatctgcgct | ctgctgaagc | cagttacctt | cggaaaaaga | gttggtagct cttgatccgg | 1860 |
| caaacaaacc | accgctggta | gcggtggttt | ttttgtttgc | aagcagcaga ttacgcgcag | 1920 |

-continued

```
aaaaaaagga tctcaagaag atcctttgat cttttctacg gggtctgacg ctcagtggaa    1980
cgaaaactca cgttaaggga ttttggtcat gagattatca aaaggatctt tcacctagat    2040
ccttttaaat taaaaatgaa gttttaaatc aatctaaagt atatatgagt aaacttggtc    2100
tgacagttac caatgcttaa tcagtgaggc acctatctca gcgatctgtc tatttcgttc    2160
atccatagtt gcctgactcc ccgtcgtgta gataactacg atacgggagg gcttaccatc    2220
tggccccagt gctgcaatga taccgcgaga cccacgctca ccggctccag atttatcagc    2280
aataaaccag ccagccggaa gggccgagcg cagaagtggt cctgcaactt tatccgcctc    2340
catccagtct attaattgtt gccgggaagc tagagtaagt agttcgccag ttaatagttt    2400
gcgcaacgtt gttggcattg ctacaggcat cgtggtgtca cgctcgtcgt ttggtatggc    2460
ttcattcagc tccggttccc aacgatcaag gcgagttaca tgatccccca tgttgtgcaa    2520
aaaagcggtt agctccttcg gtcctccgat cgttgtcaga agtaagttgg ccgcagtgtt    2580
atcactcatg gttatggcag cactgcataa ttctcttact gtcatgccat ccgtaagatg    2640
cttttctgtg actggtgagt actcaaccaa gtcattctga ataccgcgc ccggcgacc    2700
gagttgctct tgcccggcgt caatacggga taatagtgta tgacatagca gaactttaaa    2760
agtgctcatc attggaaaac gttcttcggg gcgaaaactc tcaaggatct taccgctgtt    2820
gagatccagt tcgatgtaac ccactcgtgc acccaactga tcttcagcat cttttacttt    2880
caccagcgtt tctgggtgag caaaaacagg aaggcaaaat gccgcaaaaa agggaataag    2940
ggcgacacgg aaatgttgaa tactcatact cttcctttt caatattatt gaagcattta    3000
tcagggttat tgtctcatga gcggatacat atttgaatgt atttagaaaa ataaacaaat    3060
aggggttccg cgcacatttc cccgaaaagt gccacctgac gtctaagaaa ccattattat    3120
catgacatta acctataaaa ataggcgtat cacgaggccc tttcgtctcg cgcgtttcgg    3180
tgatgacggt gaaaacctct gacacatgca gctcccggag acggtcacag cttgtctgta    3240
agcggatgcc gggagcagac aagcccgtca gggcgcgtca gcgggtgttg gcgggtgtcg    3300
gggctggctt aactatgcgg catcagagca gattgtactg agagtgcacc atatgcggtg    3360
tgaaataccg cacagatgcg taaggagaaa ataccgcatc aggcgaaatt gtaaacgtta    3420
atattttgtt aaaattcgcg ttaaatattt gttaaatcag ctcattttt aaccaatagg    3480
ccgaaatcgg caaaatccct tataaatcaa agaatagac cgagataggg ttgagtgttg    3540
ttccagtttg gaacaagagt ccactattaa agaacgtgga ctccaacgtc aaagggcgaa    3600
aaaccgtcta tcagggcgat ggcccactac gtgaaccatc acccaaatca agttttttgc    3660
ggtcgaggtg ccgtaaagct ctaaatcgga accctaaagg gagcccccga tttagagctt    3720
gacggggaaa gccggcgaac gtggcgagaa aggaagggaa gaaagcgaaa ggagcgggcg    3780
ctagggcgct ggcaagtgta gcggtcacgc tgcgcgtaac caccacaccc gccgcgctta    3840
atgcgccgct acagggcgcg tccattcgcc attcaggctg cgcaactgtt gggaagggcg    3900
atcggtgcgg gcctcttcgc tattacgcca gctggcgaaa gggggatgtg ctgcaaggcg    3960
attaagttgg gtaacgccag ggttttccca gtcacgacgt tgtaaaacga cggccagtga    4020
attgtaatac gactcactat agggcgaatt caaaaacccc tcaagaccc gtttagaggc    4080
cccaagggt tatgctagtg aattctgcag ggtacccggg gatcctctag agatccctcg    4140
acctcgagat ccattgtgct gg    4162
```

<210> SEQ ID NO 2
<211> LENGTH: 4393

<212> TYPE: DNA
<213> ORGANISM: Artificial Sequence
<220> FEATURE:
<223> OTHER INFORMATION: Description of Artificial Sequence: Plasmid pGX6

<400> SEQUENCE: 2

| | | | | | |
|---|---|---|---|---|---|
| gaattcttgg | agttgggcaa | gctctgttgg | gtggatcatc | gtgtgtcatt | agaaaaaaat | 60 |
| tctcggctag | caacttttgg | agggattgtg | taaagtatga | ttgtacagtt | tcacaataca | 120 |
| ttggagagat | ttgtcggtac | ttgttggctc | agccagttgt | ggaagaggaa | tccaggcata | 180 |
| gtgagttttg | aaagttcttt | aacttttttaa | acttttatta | aaaattgtta | ctccaggaat | 240 |
| gagattgttg | gttggaaacg | gactccgtgc | tgaaatctgg | caaccatttg | tagatcgatt | 300 |
| ccgtgtcaga | attggagaac | tttatggttc | aactgaagga | acttcatctc | tcggtatgca | 360 |
| tttttttttt | caaaagcaca | agatcgattt | accttgaact | ataaaataag | aaatatatca | 420 |
| tgcaattttt | gtaaaaatat | atttaaaaaa | ttgagaagtt | tagccaaaac | cttagatttt | 480 |
| tgcccgcttc | tgctcgtgtt | aaccgttctg | tttcaacatt | aaatctaatt | tctgccatt | 540 |
| tcagtgaaca | ttgacggaca | tgtcggagct | tgcggattct | tgccaatatc | cccattaaca | 600 |
| aagaaaatgc | atccggttcg | attaattaag | gttgatgatg | tcactggaga | agcaatccga | 660 |
| acttccgatg | gactttgcat | tgcatgtaat | ccaggagagt | ctggagcaat | ggtgtcgacg | 720 |
| atcagaaaaa | ataatccatt | attgcaattg | gagggatatc | tgaataagaa | ggaaacgaat | 780 |
| aaaaagatta | tcagagatgt | cttcgcaaag | ggagatagtt | gcttttttgac | tggagatctt | 840 |
| cttcattggg | atcgtcttgg | ttatgtatat | ttcaaggatc | gtactggaga | tactttccgt | 900 |
| tggaagggag | agaatgtgtc | gactactgaa | gtcgaggcaa | ttcttcatcc | aattactgga | 960 |
| ttgccagcac | aatggatctc | gagggatctt | ccatacctac | cagttctgcg | cctgcaggtc | 1020 |
| gcggccgcga | ctctctagac | gcgtaagctt | actagcataa | ccccttgggg | cctctaaacg | 1080 |
| ggtcttgagg | ggttttttga | gcttctcgcc | ctatagtgag | tcgtattaca | gcttgagtat | 1140 |
| tctatagtgt | cacctaaata | gcttggcgta | atcatggtca | tagctgtttc | ctgtgtgaaa | 1200 |
| ttgttatccg | ctcacaattc | cacacaacat | acgagccgga | agcataaagt | gtaaagcctg | 1260 |
| gggtgcctaa | tgagtgagct | aactcacatt | aattgcgttg | cgctcactgc | ccgctttcca | 1320 |
| gtcgggaaac | ctgtcgtgcc | agctgcatta | atgaatcggc | caacgcgcgg | ggagaggcgg | 1380 |
| tttgcgtatt | gggcgctctt | ccgcttcctc | gctcactgac | tcgctgcgct | cggtcgttcg | 1440 |
| gctgcggcga | gcggtatcag | ctcactcaaa | ggcggtaata | cggttatcca | cagaatcagg | 1500 |
| ggataacgca | ggaaagaaca | tgtgagcaaa | aggccagcaa | aaggccagga | accgtaaaaa | 1560 |
| ggccgcgttg | ctggcgtttt | tcgataggct | ccgcccccct | gacgagcatc | acaaaaatcg | 1620 |
| acgctcaagt | cagaggtggc | gaaacccgac | aggactataa | agataccagg | cgtttccccc | 1680 |
| tggaagctcc | ctcgtgcgct | ctcctgttcc | gaccctgccg | cttaccggat | acctgtccgc | 1740 |
| ctttctccct | tcgggaagcg | tggcgctttc | tcatagctca | cgctgtaggt | atctcagttc | 1800 |
| ggtgtaggtc | gttcgctcca | agctgggctg | tgtgcacgaa | ccccccgttc | agcccgaccg | 1860 |
| ctgcgcctta | tccggtaact | atcgtcttga | gtccaacccg | gtaagacacg | acttatcgcc | 1920 |
| actggcagca | gccactggta | acaggattag | cagagcgagg | tatgtaggcg | gtgctacaga | 1980 |
| gttcttgaag | tggtggccta | actacggcta | cactagaagg | acagtatttg | gtatctgcgc | 2040 |
| tctgctgaag | ccagttacct | tcggaaaaag | agttggtagc | tcttgatccg | gcaaacaaac | 2100 |
| caccgctggt | agcggtggtt | ttttttgtttg | caagcagcag | attacgcgca | gaaaaaaagg | 2160 |

-continued

```
atctcaagaa gatcctttga tcttttctac ggggtctgac gctcagtgga acgaaaactc    2220
acgttaaggg attttggtca tgagattatc aaaaaggatc ttcacctaga tcctttttaaa   2280 ttaaaaatga agttttaaat caatctaaag tatatatgag taaacttggt ctgacagtta    2340
ccaatgctta atcagtgagg cacctatctc agcgatctgt ctatttcgtt catccatagt    2400
tgcctgactc cccgtcgtgt agataactac gatacgggag ggcttaccat ctggccccag    2460
tgctgcaatg ataccgcgag acccacgctc accggctcca gatttatcag caataaacca    2520
gccagccgga agggccgagc gcagaagtgg tcctgcaact ttatccgcct ccatccagtc    2580
tattaattgt tgccgggaag ctagagtaag tagttcgcca gttaatagtt tgcgcaacgt    2640
tgttggcatt gctacaggca tcgtggtgtc acgctcgtcg tttggtatgg cttcattcag    2700
ctccggttcc caacgatcaa ggcgagttac atgatccccc atgttgtgca aaaaagcggt    2760
tagctccttc ggtcctccga tcgttgtcag aagtaagttg gccgcagtgt tatcactcat    2820
ggttatggca gcactgcata attctcttac tgtcatgcca tccgtaagat gcttttctgt    2880
gactggtgag tactcaacca agtcattctg agaataccgc gccggcgac cgagttgctc     2940 ttgcccggcg tcaatacggg ataatagtgt atgacatagc agaactttaa aagtgctcat    3000
cattggaaaa cgttcttcgg ggcgaaaact ctcaaggatc ttaccgctgt tgagatccag    3060
ttcgatgtaa cccactcgtg cacccaactg atcttcagca tcttttactt tcaccagcgt    3120
ttctgggtga gcaaaaacag gaaggcaaaa tgccgcaaaa aagggaataa gggcgacacg    3180
gaaatgttga atactcatac tcttcctttt tcaatattat tgaagcattt atcagggtta    3240
ttgtctcatg agcggataca tatttgaatg tatttagaaa aataaacaaa tagggggttcc   3300 gcgcacattt ccccgaaaag tgccacctga cgtctaagaa accattatta tcatgacatt    3360
aacctataaa aataggcgta tcacgaggcc ctttcgtctc gcgcgtttcg gtgatgacgg    3420
tgaaaacctc tgacacatgc agctcccgga gacggtcaca gcttgtctgt aagcggatgc    3480
cgggagcaga caagcccgtc agggcgcgtc agcgggtgtt ggcgggtgtc ggggctggct    3540
taactatgcg gcatcagagc agattgtact gagagtgcac catatgcggt gtgaaatacc    3600
gcacagatgc gtaaggagaa ataccgcat caggcgaaat tgtaaacgtt aatattttgt     3660
taaaattcgc gttaaatatt tgttaaatca gctcattttt taaccaatag gccgaaatcg    3720
gcaaaatccc ttataaatca aaagaataga ccgagatagg gttgagtgtt gttccagttt    3780
ggaacaagag tccactatta aagaacgtgg actccaacgt caaagggcga aaaccgtct    3840 atcagggcga tggcccacta cgtgaaccat cacccaaatc aagttttttg cggtcgaggt    3900
gccgtaaagc tctaaatcgg aaccctaaag ggagcccccg atttagagct tgacgggaa    3960 agccggcgaa cgtggcgaga aaggaaggga agaaagcgaa aggagcgggc gctagggcgc    4020
tggcaagtgt agcggtcacg ctgcgcgtaa ccaccacacc cgccgcgctt aatgcgccgc    4080
tacagggcgc gtccattcgc cattcaggct gcgcaactgt tgggaagggc gatcggtgcg    4140
ggcctcttcg ctattacgcc agctggcgaa agggggatgt gctgcaaggc gattaagttg    4200
ggtaacgcca gggttttccc agtcacgacg ttgtaaaacg acggccagtg aattgtaata    4260
cgactcacta tagggcgaat tcaaaaaacc cctcaagacc cgtttagagg ccccaagggg    4320
ttatgctagt gaattctgca gggtacccgg ggatcctcta gagatccctc gacctcgaga    4380
tccattgtgc tgg                                                      4393
```

<210> SEQ ID NO 3

```
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide oGN87

<400> SEQUENCE: 3
gtgaaggtta caaatgggc gacgttgtcg                                  30

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide oGN88

<400> SEQUENCE: 4
cgtcacagcg acacagtaca ttggagaaat c                               31

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide oGN89

<400> SEQUENCE: 5
gaattcttgg agttgggcaa gctctgttgg                                 30

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide oGN90

<400> SEQUENCE: 6
cgaggcaatt cttcatccaa ttactggatt g                               31
```